United States Patent [19]

Koda et al.

[11] Patent Number: 4,556,737

[45] Date of Patent: Dec. 3, 1985

[54] SULFONIUM COMPOUNDS, PROCESSES FOR PREPARING THE COMPOUNDS AND PHARMACOLOGICAL COMPOSIITONS CONTAINING THE SAME

[75] Inventors: Akihide Koda; Mikio Hori; Naosuke Matsuura, all of Gifu; Mitsugi Yasumoto, Tokushima; Ichiro Yamawaki, Tokushima; Shuichi Ueda, Tokushima; Yukio Tada, Tokushima, all of Japan

[73] Assignee: Taiho Pharmaceutical Company Limited, Tokyo, Japan

[21] Appl. No.: 583,674

[22] Filed: Feb. 27, 1984

[30] Foreign Application Priority Data

Mar. 11, 1983 [JP]  Japan ................................. 58-41184
Mar. 16, 1983 [JP]  Japan ................................. 58-44777
Jan. 18, 1984 [JP]  Japan ................................. 59-7731

[51] Int. Cl.$^4$ .................. C07C 103/12; C07C 148/00; C07C 43/20; C07C 41/18
[52] U.S. Cl. .................................... 564/218; 260/398; 260/463; 560/250; 564/223; 568/648
[58] Field of Search ................ 564/191, 192, 215, 218, 564/223; 424/311, 320

[56] References Cited

U.S. PATENT DOCUMENTS 3,350,447 10/1967 Ratts ................................... 564/192
3,478,154 11/1969 Ratts ................................... 424/320

FOREIGN PATENT DOCUMENTS 3105303 12/1981 Fed. Rep. of Germany .
147930 11/1979 Japan .
140762  8/1982 Japan .
142914  9/1982 Japan .

OTHER PUBLICATIONS

Taiho Yakuhin Kogyo, *Chemical Abstracts*, 98:53385j (1983).

*Primary Examiner*—Donald G. Daus
*Assistant Examiner*—Stephen M. Kapner
*Attorney, Agent, or Firm*—Murray, Whisenhunt and Ferguson

[57] ABSTRACT

This invention provides novel sulfonium compounds, processes for the preparation of the sulfonium compounds, and pharmacological composition containing the sulfonium compound. The compounds of this invention are useful for treating allergy.

9 Claims, No Drawings

SULFONIUM COMPOUNDS, PROCESSES FOR PREPARING THE COMPOUNDS AND PHARMACOLOGICAL COMPOSIITONS CONTAINING THE SAME

This invention relates to novel sulfonium compounds, processes for preparing the compounds and pharmacological compositions containing such compounds.

The sulfonium compounds of this invention are represented by the formula

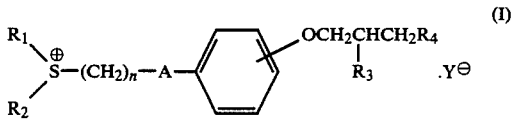

wherein $R_1$ and $R_2$ are the same or different and are each alkyl having 1 to 6 carbon atoms; $R_3$ is hydrogen, hydroxy, alkoxy having 1 to 6 carbon atoms, acyloxy having 2 to 6 carbon atoms, benzoyloxy, carboxyethylcarbonyloxy, alkoxycarbonyloxy having 2 to 5 carbon atoms, phenoxycarbonyloxy, acylacetyloxy having 4 to 6 carbon atoms, alkoxyacetyloxy having 3 to 6 carbon atoms, acylaminoacetyloxy having 4 to 6 carbon atoms, phenoxyacetyloxy, phenylalkyloxy having 7 to 10 carbon atoms, phenylalkyloxycarbonyloxy having 8 to 11 carbon atoms, phenylalkyloxymethoxy having 8 to 11 carbon atoms or lactoyloxy; $R_4$ is hydrogen, hydroxy, alkoxy having 1 to 6 carbon atoms, acyloxy having 2 to 6 carbon atoms, cycloalkyloxy having 5 to 7 carbon atoms, phenoxy, benzoyloxy, alkoxycarbonyloxy having 2 to 5 carbon atoms, ethoxy substituted with alkoxy having 1 to 6 carbon atoms, tetrahydrofurfuryloxy, tetrahydropyranylmethyloxy, carbamoyloxy, alkylcarbamoyloxy having 2 to 5 carbon atoms, phenylcarbamoyloxy or phenylalkyloxycarbonyloxy having 8 to 11 carbon atoms; Y is an acid residue; A is —O— or —CONH— and n is an integer of 1 to 3; with the proviso that $R_3$ and $R_4$ are not both hydrogen at the same time.

Examples of alkyl groups having 1 to 6 carbon atoms represented by $R_1$ and $R_2$ of the formula (I) are methyl, ethyl, propyl, isopropyl, butyl, isobutyl, t-butyl, pentyl hexyl, etc.

Examples of the groups represented by $R_3$ are as follows. Exemplary of alkoxy groups having 1 to 6 carbon atoms are methoxy, ethoxy, propyloxy, isopropyloxy, butoxy, hexyloxy, etc. Representative of acyloxy groups having 2 to 6 carbon atoms are acetyloxy, propionyloxy, butyryloxy, pivaloyloxy, caproyloxy, etc. Illustrative of alkoxycarbonyloxy groups having 2 to 5 carbon atoms are methoxycarbonyloxy, ethoxycarbonyloxy, propyloxycarbonyloxy, butoxycarbonyloxy, isobutoxycarbonyloxy, t-butoxycarbonyloxy, etc. Exemplary of acylacetyloxy groups having 4 to 6 carbon atoms are acetylacetyloxy, propionylacetyloxy, butyrylacetyloxy and like lower alkylcarbonylacetyloxy groups, etc. Representative of alkoxyacetyloxy groups having 3 to 6 carbon atoms are methoxyacetyloxy, ethoxyacetyloxy, propoxyacetyloxy, butoxyacetyloxy, etc. Illustrative of acylaminoacetyloxy groups having 4 to 6 carbon atoms are acetylaminoacetyloxy, proionylaminoacetyloxy, butyrylaminoacetyloxy and like lower alkylcarbonylaminoacetyloxy groups, etc. Exemplary of phenylalkyloxy groups having 7 to 10 carbon atoms are benzyloxy, phenethyloxy, phenylpropyloxy, phenylbutyloxy, etc. Representative of phenylalkyloxycarbonyloxy groups having 8 to 11 carbon atoms are benzyloxycarbonyloxy, phenethyloxycarbonyloxy, phenylpropyloxycarbonyloxy, phenylbutyloxycarbonyloxy, etc. Illustrative of phenylalkyloxymethoxy groups having 8 to 11 carbon atoms are benzyloxymethoxy, phenethyloxymethoxy, phenylpropyloxymethoxy, phenylbutyloxymethoxy, etc.

Examples of the groups represented by $R_4$ are as follows. Exemplary of alkoxy groups having 1 to 6 carbon atoms are methoxy, ethoxy, propyloxy, isopropyloxy, butoxy, hexyloxy, etc. Representative of acyloxy groups having 2 to 6 carbon atoms are acetyloxy, propionyloxy, butyryloxy, pivaloyloxy, caproyloxy, etc. Illustrative of cycloalkyloxy groups having 5 to 7 carbon atoms are cyclopentyloxy, cyclohexyloxy, cycloheptyloxy, etc. Exemplary of alkoxycarbonyloxy groups having 2 to 5 carbon atoms are methoxycarbonyloxy, ethoxycarbonyloxy, propyloxycarbonyloxy, butoxycarbonyloxy, isobutoxycarbonyloxy, t-butoxycarbonyloxy, etc. Representative of the alkoxy groups in the ethoxy groups substituted with $C_{1-6}$ alkoxy groups are the same as those exemplified above. Illustrative of alkylcarbamoyloxy groups having 2 to 5 carbon atoms are methylcarbamoyloxy, ethylcarbamoyloxy, propylcarbamoyloxy, butylcarbamoyloxy, etc. Exemplary of phenylalkyloxycarbonyloxy groups having 8 to 11 carbon atoms are benzyloxycarbonyloxy, phenethyloxycarbonyloxy, phenylpropyloxycarbonyloxy, phenylbutyloxycarbonyloxy, etc.

The acid residues represented by Y in the formula (I) are protonic acid residues which are pharmaceutically acceptable. Examples of such acid residues are residues of inorganic acid such as hydrogen chloride, hydrogrn iodide, hydrogen bromide, tetrafluoroboric acid, perchloric acid, phosphoric acid, sulfuric acid, nitric acid, metaphosphoric acid and the like, and residues of organic acid such as methanesulfonic acid, benzenesulfonic acid, toluenesulfonic acid, camphorsulfonic acid, 1,5-naphthalenedisulfonic acid, picrylsulfonic acid, cyclohexylsulfamic acid and like organic sulfonic acid, and lactic acid, maleic acid, malonic acid, fumaric acid, butyric acid, ascorbic acid, linoleic acid, lauric acid, palmitic acid, stearic acid, oleic acid, propionic acid, citric acid, acetic acid, formic acid, nicotinic acid, succinic acid and like carboxylic acid.

A preferred class of the present compounds of the formula (I) are those wherein $R_1$, $R_2$, n, A and Y are as defined above, $R_3$ is hydrogen, hydroxy, alkoxy having 1 to 6 carbon atoms, acyloxy having 2 to 6 carbon atoms, carboxyethylcarbonyloxy, benzoyloxy, alkoxycarbonyloxy having 2 to 5 carbon atoms or phenoxycarbonyloxy, and $R_4$ is hydrogen, hydroxy, alkoxy having 1 to 6 carbon atoms, cycloalkyloxy having 5 to 7 carbon atoms, phenoxy, acyloxy having 2 to 6 carbon atoms, benzoyloxy, ethoxy substituted with $C_{1-6}$ alkoxy, tetrahydrofurfuryloxy, tetrahydropyranylmethyloxy or carbamoyloxy.

More preferable of the foregoing class are those wherein $R_1$ and $R_2$ are as defined above, $R_3$ is hydrogen, hydroxy, alkoxy having 1 to 6 carbon atoms, acyloxy having 2 to 6 carbon atoms, carboxyethylcarbonyloxy, benzoyloxy, alkoxycarbonyloxy having 2 to 5 carbon atoms or phenoxycarbonyloxy, $R_4$ is hydrogen, hydroxy, alkoxy having 1 to 6 carbon atoms, cycloalkyloxy having 5 to 7 carbon atoms, phenoxy, acyloxy having 2 to 6 carbon atoms or benzoyloxy, A is —CONH— and n and Y are as defined above. Also more preferable compounds are those wherein $R_1$ and $R_2$ are as defined above, $R_3$ is hydrogen, hydroxy, alkoxy having 1 to 6 carbon atoms, acyloxy having 2 to 6 carbon atoms or benzoyloxy, $R_4$ is hydrogen, hydroxy, alkoxy having 1 to 6 carbon atoms, ethoxy substituted with $C_{1-6}$ alkoxy, tetrahydrofurfuryloxy, tetrahydropyranylmethyloxy, phenoxy, carbamoyloxy, acyloxy having 2 to 6 carbon atoms or benzoyloxy, A is —O—, and n and Y are as defined above.

The present compounds of the formula (I) also include another class of compounds wherein $R_1$ and $R_2$ are as defined above, $R_3$ is acylacetyloxy having 4 to 6 carbon atoms, alkoxyacetyloxy having 3 to 6 carbon atoms, acylaminoacetyloxy having 4 to 6 carbon atoms, phenoxyacetyloxy, phenylalkyloxy having 7 to 10 carbon atoms, phenylalkyloxycarbonyloxy having 8 to 11 carbon atoms, phenylalkyloxymethoxy having 8 to 11 carbon atoms, alkoxycarbonyloxy having 2 to 5 carbon atoms or lactoyloxy, $R_4$ is alkoxy having 1 to 6 carbon atoms, phenoxy, alkoxycarbonyloxy having 2 to 5 carbon atoms, phenylalkyloxycarbonyloxy having 8 to 11 carbon atosm, alkylcarbamoyloxy having 2 to 5 carbon atoms or phenylcarbamoyloxy, and A is —CONH—, and n and Y are as defined above.

The sulfonium compounds of the invention represented by the formula (I) have anti-allergic activity and are useful for treating diseases induced by type I allergy reaction. For example, the present compounds are useful for treating bronchial asthma, allergic rhinitis, drug allergy, etc.

Processes for preparing the present compounds of the formula (I) will be described below. Various processes are available for producing the compounds (I). For example, the compounds (I) can be prepared by the following processes.

Process A

A sulfide compound represented by the formula

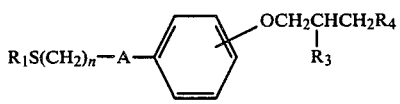
(II)

wherein $R_1$, $R_3$, $R_4$, A and n are as defined above is reacted with a compound of the formula $$R_2Y \quad \text{(III)}$$

wherein $R_2$ and Y are as defined above.

The reaction is conducted in the presence or absence of a solvent at a temperature of about −30° to about 150° C., preferably about 0° to about 100° C., and is completed in about 0.5 to about 72 hours. The compound (III) is used in an excess amount relative to the sulfide compound (II), preferably in an amount (mole) of about 1 to about 4 times the theoretical amount per mole of the compound (II). Useful solvents include, for example, methanol, ethanol, propanol and like alcohols; acetonitrile, nitromethane, dimethylformamide, dimethyl sulfoxide and like polar solvents; methylene chloride, chloroform and like halogenated hydrocarbons; benzene, toluene, xylene and like aromatic hydrocarbons; ethyl ether, propyl ether and like ethers; acetone; petroleum ether; ethyl acetate; water; etc. The solvents are used singly or in mixture. The reaction can be carried out in a sealed container, when required.

Of the sulfide compounds (II) serving as the starting material, the compounds represented by the formula

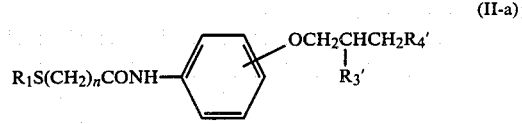
(II-a)

wherein $R_1$ and n are as defined above, $R_3'$ is hydrogen, hydroxy, alkoxy having 1 to 6 carbon atoms, acyloxy having 2 to 6 carbon atoms, benzoyloxy, carboxyethylcarbonyloxy, alkoxycarbonyloxy having 2 to 5 carbon atoms, or phenoxycarbonyloxy, and $R_4'$ is hydrogen, hydroxy, alkoxy having 1 to 6 carbon atoms, acyloxy having 2 to 6 carbon atoms, cycloalkyloxy having 5 to 7 carbon atoms, phenoxy, or benzoyloxy can be prepared, for example, by reacting a compound of the formula

(IV-a)

wherein $R_1$ and n are as defined above and hal is halogen with a compound of the formula

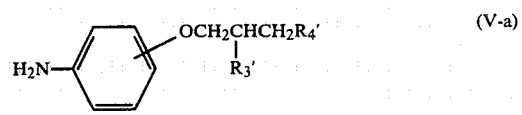
(V-a)

wherein $R_3'$ and $R_4'$ are as defined above.

Of the sulfide compounds (II), a compound of the formula

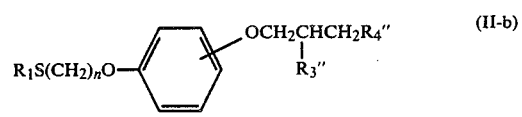
(II-b)

wherein $R_1$ and n are as defined above, $R_3''$ is hydrogen, hydroxy, alkoxy having 1 to 6 carbon atoms, acyloxy having 2 to 6 carbon atoms or benzoyloxy, $R_4''$ is hydrogen, hydroxy, alkoxy having 1 to 6 carbon atoms, ethoxy substituted with $C_{1-6}$ alkoxy, tetrahydrofurfuryloxy, tetrahydropyranylmethyloxy, phenoxy, carbamoyloxy, acyloxy having 2 to 6 carbon atoms or benzoyloxy can be prepared, for example, by reacting a compound of the formula

(IV-b)

wherein $R_1$ and n are as defined above and hal is a halogen atom with a compound of the formula

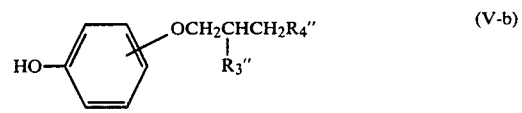
(V-b)

wherein $R_3''$ and $R_4''$ are as defined above.

The reaction between the compound (IV-a) and the compound (V-a) and the reaction between the compound (IV-b) and the compound (V-b) are both performed preferably in the presence of a basic compound such as sodium, potassium or like alkali metal, alkali metal hydride, alkali metal hydroxide or alkali metal carbonate or pyridine, morpholine, piperidine, piperazine, triethylamine or the like in a suitable solvent or in the absence of a solvent at a temperature of about 0° to about 200° C. Reference Examples to be given later will describe in detail the synthesis of the sulfide compounds (II-a) and (II-b).

Of the sulfide compounds (II), a compound of the formula

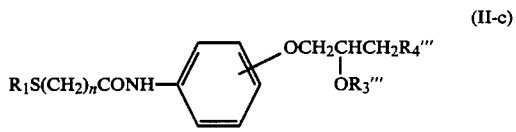

(II-c)

wherein $R_1$ and n are as defined above, $R_3'''$ is acylacetyl having 4 to 6 carbon atoms, alkoxyacetyl having 3 to 6 carbon atoms, acylaminoacetyl having 4 to 6 carbon atoms, phenoxyacetyl, phenylalkyl having 7 to 10 carbon atoms, phenylalkyloxycarbonyl having 8 to 11 carbon atoms, phenylalkyloxymethyl having 8 to 11 carbon atoms, alkoxycarbonyl having 2 to 5 carbon atoms or lactoyl, and $R_4'''$ is alkoxy having 1 to 6 carbon atoms, phenoxy, alkoxycarbonyloxy having 2 to 5 carbon atoms, phenylalkyloxycarbonyloxy having 8 to 11 carbon atoms, alkylcarbamoyloxy having 2 to 5 carbon atoms or phenylcarbamoyloxy can be prepared, for example, by reacting a compound of the formula

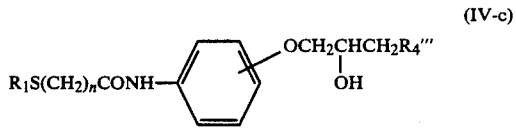

(IV-c)

wherein $R_1$, $R_4'''$ and n are as defined above with a compound of the formula

(V-c)

wherein $R_3'''$ is as defined above and Hal is halogen in the presence of a suitable solvent or in the absence of a solvent at a temperature in the range of about 0° to about 100° C. Preferably the reaction is effected in the presence of a basic compound such as sodium, potassium or like alkali metal, hydride or hydroxide of alkali metal, pyridine, morpholine, piperidine, piperazine, triethylamine or the like. The synthesis of the sulfide compound (II-c) will be stated in detail in Reference Examples to be given later.

Process B

A sulfonium halide of the formula

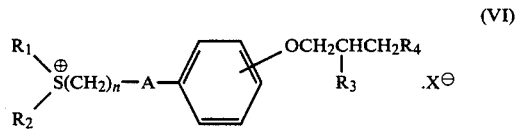

(VI)

wherein $R_1$, $R_2$, $R_3$, $R_4$, A and n are as defined above and X is halogen is reacted with a compound of the formula

ZY$_1$ (VII)

wherein Z is a silver atom or alkali metal atom and $Y_1$ is an acid residue different from a halogen represented by X.

This process utilizes the salt exchange reaction of the sulfonium halide (VI) (the present compound of the formula (I) wherein Y is a hydrohalogenic acid residue). The starting material, i.e. the sulfonium halide (VI), is prepared according to Process A, and can be advantageously used as contained in the resulting reaction mixture without isolation therefrom. It can be employed, of course, after separation from the reaction mixture and purification.

Useful compounds (VII) include silver salts or alkali metal salts of acids which are capable of giving the acid residue represented by Y in the formula (I). Examples of useful acids are hydrogen chloride, hydrogen iodide, hydrogen bromide, tetrafluoroboric acid, perchloric acid, phosphoric acid, sulfuric acid, nitric acid, metaphosphoric acid and the like, and residues of organic acid such as methanesulfonic acid, benzenesulfonic acid, toluenesulfonic acid, camphorsulfonic acid, 1,5-naphthalenedisulfonic acid, picrylsulfonic acid, cyclohexylsulfamic acid and like organic sulfonic acid, and lactic acid, maleic acid, malonic acid, fumaric acid, butyric acid, ascorbic acid, linoleic acid, lauric acid, palmitic acid, stearic acid, oleic acid, propionic acid, citric acid, acetic acid, formic acid, nicotinic acid, succinic acid and like carboxylic acid. Exemplary of useful alkali metals are sodium, potassium, lithium, etc.

The salt exchange reaction of this process is conducted in a solvent at a temperature of usually about −30° to about 150° C., preferably about 0° to about 100° C. The preferred amount of the compound (VII) is about 1 to 4 times the theoretical amount of the sulfonium halide (VI). Useful solvents can be any of those exemplified above as usable in the reaction of Process A.

Process C

This process also utilizes salt exchange reaction and comprises reacting the sulfonium halide (VI) with a silver oxide and a compound of the formula

HY$_1$ (VIII)

wherein $Y_1$ is as defined above.

Examples of the sulfonium halides (VI) to be used as the starting material are those already mentioned above in Process B. Useful compounds (VIII) are free organic or inorganic acids capable of forming the acid residue represented by Y in the formula (I). Exemplary of such compounds are those stated above in Process B.

The silver oxide is used in the reaction in an amount of usually more than 1 mole, preferably about 1 to about 4 moles, per mole of the sulfonium halide (VI). The amount of the compound (VIII) is more than 1 mole, preferably about 1 to about 4 moles, per mole of the sulfonium halide (VI). The reaction of this process is effected in a solvent at a temperature of usually about −30° to about 150° C., preferably about 0° to about 100° C. The solvents useful in the reaction of Process A are usable in this reaction.

While the reaction of this process can be performed by placing the sulfonium halide (VI), silver oxide and compound (VIII) in a suitable reactor at the same time, it is preferred to use a two-stage method comprising the steps of reacting the sulfonium halide and the silver oxide to give a sulfonium hydroxide of the formula (IX)

as an intermediate and subsequently placing the compound (VIII) in the reactor to further react with the sulfonium hydroxide. This reaction is shown by the following reaction equation.

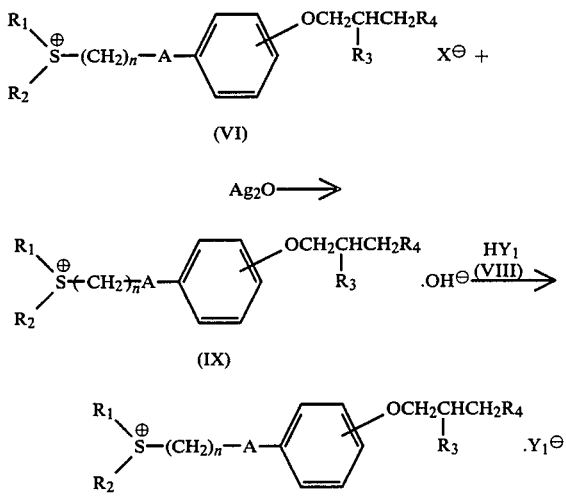

In the foregoing formulae, $R_1$, $R_2$, $R_3$, $R_4$, n, A, $Y_1$ and X are as defined above.

The silver oxide to be used in this reaction is employed in an amount of usually more than 1 mole, preferably about 1 to about 4 moles, per mole of the sulfonium halide (VI). The amount of the acid (VIII) is over 1 mole, preferably about 1 to about 4 moles, per mole of the sulfonium hydroxide (IX). The same solvents exemplified above in Process A are usuable in the reaction of this process. The reaction between the sulfonium halide (VI) and the silver oxide and the reaction between the sulfonium hydroxide (IX) and the compound (VIII) are both conducted at a temperature of usually about $-30°$ to about 150° C., preferably about 0° to about 100° C.

The sulfonium compound of the present invention prepared by Process A to C can be isolated from the reaction mixture by a usual separation method such as recrystallization, extraction, concentration, column chromatography or the like.

The compounds of the invention have an immunoregulatory action in addition to the above-mentioned anti-allergic activity, and are useful as an active component of drugs.

For use as drugs, the compounds of the present invention can be given in the form of pharmacological compositions having various dosage forms, such as oral preparation, injection, rectal suppository or inhalant, in accordance with the purpose of therapy contemplated. Such preparations can be formulated in the manner already known in the art, using conventional pharmacologically acceptable, non-toxic carriers or excipients. For the formulation of solid preparations for oral administration, such as tablets, coated tablets, granules, powders and capsules, excipients and, when required, binders, disintegrators, lubricants or glazes, coloring agents, corrigents, etc. can be added to the compound of this invention. Such additives are already known in the art and useful examples are excipients such as lactose, white sugar, sodium chloride, glucose solution, starch, calcium carbonate, kaolin, crystalline cellulose and silicic acid; binders such as water, ethanol, propanol, glucose, carboxymethylcellulose, shellac, methylcellulose, potassium phosphate and polyvinylpyrrolidone; disintegrators such as dried starch, sodium alginate, agar powder, sodium hydrogencarbonate, calcium carbonate, sodium lauryl sulfate, glyceryl monostearate, starch and lactose; lubricants or glazes such as purified talc, steraric acid salt, boric acid powder, solid polyethylene glycol; corrigents such as sucrose, compound bitter orange peel, citric acid, tartaric acid, etc. For the formulation of liquid preparations for oral administration, such as solutions for oral administration, syrups, etc., conventional corrigents, buffers, stabilizers, etc. can be added to the present compound. Such preparations can be formulated in the usual manner. Examples of useful corrigents are those exemplified above. Typical buffers include sodium citrate. Stabilizers include tragacanth, gum arabic, gelatin, etc. The pharmacological compositions thus prepared are orally administered. Parenteral solutions can be formulated in the usual manner using distilled water for injection as the carrier and adding to the present compound conventional additives such as pH-adjusting agents, buffers, stabilizers, isotonic agents, local anesthetics, etc. Examples of the pH-adjusting agents and buffers are sodium salts of citric acid, acetic acid and phosphoric acid. The stabilizers include sodium pyrosulfite (anti-oxidant), EDTA, thioglycolic acid, thiolactic acid, etc. Examples of useful local anesthetics are procaine hydrochloride, xylocaine hydrochloride, lidocaine hydrochloride, etc. Such solutions can be given subcutaneously, intramascularly or intravenously. For the preparation of rectal suppositories, conventional excipients and if required, surfactants, etc. can be added to the present compound, followed by formulation in the usual manner. Such suppositories are administered to the rectum. Inhalants can be prepared in the usual manner by adding to the present compound a conventional propellant such as flon gas, etc., and other conventional additives, if desired.

The amount of the present compound to be incorporated into the foregoing preparations varies with the symptoms of the patient or with the type of the preparation. Preferably the amount per administration unit is about 5 to about 1000 mg for oral administration, about 0.1 to about 500 mg for parenteral administration, about 5 to about 1000 mg for intrarectal administration and about 1 to about 500 mg for inhalant administration. The dosage per day for an adult, which is variable with the symptoms and the like, is preferably about 0.1 to about 5000 mg for usual purposes.

For a better understanding of the present invention, given below are reference examples for producing sulfide compounds (II) used as the starting material for the preparation of the present compounds and examples for preparing the present compounds.

REFERENCE EXAMPLE 1

Synthesis of 4-(3-ethoxy-2-hydroxypropoxy)phenylcarbamoylmethyl methyl sulfide

Dissolved in 4 ml of dimethylformamide were 2.00 g of triethylamine and 2.11 g of 4-(3-ethoxy-2-hydroxypropoxy)aniline. To the solution was added 1.25 g of methylmercaptoacetyl chloride with ice-cooling and the mixture was stirred at room temperature for 12 hours. The reaction mixture was concentrated and the residue was extracted with chloroform. The chloroform layer was washed with water and concentrated. The resulting residue was purified by silica gel column chromatography using a 1:5 ethanol-chloroform mixture, giving 2.85 g of 4-(3-ethoxy-2-hydroxypropoxy)phenylcarbamoylmethyl methyl sulfide in 95.3% yield.

NMR (DMSO-d$_6$, δ value, ppm):
1.15 (3H, CH$_3$CH$_2$O—), 2.19 (3H, CH$_3$S—), 3.33 (2H, —SCH$_2$—), 3.9–4.3

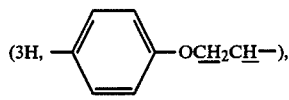

6.89, 7.46

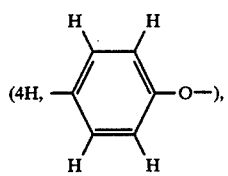

8.30 (1H, CONH).

REFERENCE EXAMPLE 2

Synthesis of 2-{4-(3-ethoxy-2-hydroxypropoxy)phenylcarbamoyl}ethyl methyl sulfide Dissolved in 4 ml of dimethylformamide were 1.46 g of triethylamine and 1.52 g of 4-(3-ethoxy-2-hydroxypropoxy)aniline. A 1.10 g quantity of 3-methylmercaptopropionyl chloride was added to the solution with ice-cooling. The mixture was stirred at room temperature for 12 hours and the reaction mixture was concentrated. The residue was extracted with chloroform and the chloroform layer was washed successively with 1N hydrochloric acid, a saturated aqueous solution of sodium hydrogencarbonate and water and concentrated. Ether was added to the residue and the crystals formed were filtered off to give 1.52 g of 2-{4-(3-ethoxy-2-hydroxypropoxy)phenylcarbamoyl}ethyl methyl sulfide in 67.4%, M.P. 79° to 81° C.

EXAMPLE 1

Synthesis of 4-(3-ethoxy-2-hydroxypropoxy)phenylcarbamoylmethyldimethylsulfonium p-toluenesulfonate (Compound 1)

Dissolved in 20 ml of methylene chloride was 2.99 g of 4-(3-ethoxy-2-hydroxypropoxy)phenylcarbamoylmethyl methyl sulfide. To the solution was added 5.50 g of methyl p-toluenesulfonate. The mixture was stirred at room temperature for 24 hours and ether was added to the reaction mixture. The insoluble solid was filtered off and recrystallized from methylene chloride-ether, giving 4.75 g of 4-(3-ethoxy-2-hydroxypropoxy)phenylcarbamoylmethyldimethylsulfonium p-toluenesulfonate (Compound 1) in 97.7% yield, M.P. 139° to 141° C.

EXAMPLE 2

The procedure of Example 1 was repeated by using appropriate starting materials, producing Compounds 8, 12, 16, 27, 28, 32 and 34 as shown in Table 1 to be given later.

EXAMPLE 3

Synthesis of 4-(2-acetoxy-3-ethoxypropoxy)phenylcarbamoylmethyldimethylsulfonium p-toluenesulfonate (Compound 2)

A 7 g quantity of methyl p-toluenesulfonate was added to 3.41 g of 4-(2-acetoxy-3-ethoxypropoxy)phenylcarbamoylmethyl methyl sulfide. The mixture was stirred at room temperature for 8 hours. Ether was added to the reaction mixture and the insoluble solid was filtered off, and recrystallized from ethanol-ether, giving 5.10 g of 4-(2-acetoxy-3-ethoxypropoxy)phenylcarbamoylmethyldimethylsulfonium p-toluenesulfonate (Compound 2) in 96.6% yield, M.P. 100° to 105° C.

EXAMPLE 4

Using appropriate starting materials, the procedure of Example 3 was followed to afford Compounds 5, 6, 17, 18, 19, 21, 22, 25, 26, 29, 33, 73, 74 and 77 as shown in Table 1 below.

EXAMPLE 5

Synthesis of 2-{4-(2,3-dihydroxypropoxy)phenylcarbamoyl}ethyldimethylsulfonium iodide (Compound 3)

Dissolved in 5 ml of dimethylformamide was 2.85 g of 2-{4-(2,3-dihydroxypropoxy)phenylcarbamoyl}ethyl methyl sulfide. To the solution was added 5.00 g of methyl iodide and the mixture was stirred at room temperature for 12 hours. Ether was added to the reaction mixture and the insoluble solid was filtered off, and recrystallized from methanol-ether, giving 4.05 g of 2-{4-(2,3-dihydroxypropoxy)phenylcarbamoyl}ethyldimethylsulfonium iodide (Compound 3) in 94.8% yield, M.P. 113° to 115° C.

EXAMPLE 6

Using suitable starting materials, the procedure of Example 5 was repeated to afford Compounds 9, 13, 35, 37, 75 and 76 as shown in Table 1 below.

EXAMPLE 7

Synthesis of 2-{4-(2,3-dihydroxypropoxy)phenylcarbamoyl}ethyldimethylsulfonium p-toluenesulfonate (Compound 4)

Dissolved in 20 ml of acetonitrile was 2.85 g of 2-{4-(2,3-dihydroxypropoxy)phenylcarbamoyl}ethyldimethylsulfonium iodide produced in Example 5. To the solution was added 2.79 g of silver p-toluenesulfonate. The mixture was stirred at room temperature for 1 hour. The reaction mixture was filtered, and hydrogen sulfide and activated charcoal were added to the filtrate. The resulting mixture was filtered and the filtrate was concentrated and the residue was purified using methylene chloride-ether, giving 4.11 g of 2-{4-(2,3-dihydroxypropoxy)phenylcarbamoyl}ethyldimethylsulfonium p-toluenesulfonate (Compound 4) in 96.3% yield.

EXAMPLE 8

The procedure of Example 7 was repeated using suitable starting materials, producing Compounds 10, 36 and 38 as shown in Table 1 to be given later.

EXAMPLE 9

Synthesis of 2-{4-(3-butoxy-2-hydroxypropoxy)phenylcarbamoyl}ethyldimethylsulfonium p-toluenesulfonate (Compound 14)

Dissolved in 20 ml of methanol was 4.83 g of 2-{4-(3-butoxy-2-hydroxypropoxy)phenylcarbamoyl}ethyldimethylsulfonium iodide produced in Example 6. To the solution was added 2.31 g of silver oxide and the resulting mixture was stirred at room temperature for 1 hour. The reaction mixture was filtered and to the filtrate was added a solution of 3.44 g of p-toluenesulfonic acid in 5 ml of methanol. The mixture was concentrated and the residue was purified using acetonitrile-ether, giving 5.10 g of 2-{4-(3-butoxy-2-hydroxypropoxy)phenylcarbamoyl}ethyldimethylsulfonium p-toluenesulfonate (Compound 14) in 96.6% yield.

EXAMPLE 10

Synthesis of 2-{4-(2-hydroxy-3-propoxypropoxy)phenylcarbamoyl}ethyldimethylsulfonium picrylsulfonate (Compound 11)

Dissolved in 5 ml of water was 4.69 g of 2-{4-(2-hydroxy-3-propoxypropoxy)phenylcarbamoyl}ethyldimethylsulfonium iodide produced in Example 6. To the solution was added a solution of 6 g of sodium picrylsulfonate in 10 ml of water. The crystals formed were filtered-off, giving 6.11 g of 2-{4-(2-hydroxy-3-propoxypropoxy)phenylcarbamoyl}ethyldimethylsulfonium picrylsulfonate (Compound 11) in 96.2% yield, M.P. 117° to 119° C.

EXAMPLE 11

Synthesis of 2-{4-(3-butoxy-2-hydroxypropoxy)phenylcarbamoyl}ethyldimethylsulfonium picrylsulfonate (Compound 15)

Dissolved in 5 ml of water was 5.28 g of 2-{4-(3-butoxy-2-hydroxypropoxy)phenylcarbamoyl}ethyldimethylsulfonium p-toluenesulfonate. To the solution was added a solution of 9 g of sodium picrylsulfonate in 10 ml of water. The crystals separating out were filtered off and recrystallized from ethanol, giving 6.50 g of 2-{4-(3-butoxy-2-hydroxypropoxy)phenylcarbamoyl}ethyldimethylsulfonium picrylsulfonate (Compound 15) in 93.5% yield, M.P. 106° to 108° C.

EXAMPLE 12

Synthesis of 2-{4-(2-hydroxy-3-methoxypropoxy)phenylcarbamoyl}ethyldimethylsulfonium p-toluenesulfonate (Compound 7)

A 4.00 g quantity of methyl iodide and then 2.79 g of silver p-toluenesulfonate were added to a solution of 2.99 g of 2-{4-(2-hydroxy-3-methoxypropoxy)phenylcarbamoyl}ethyl methyl sulfide in 30 ml of methylene chloride. The mixture was stirred at room temperature for 12 hours. The reaction mixture was filtered, and hydrogen sulfide and activated charcoal were added to the filtrate. The mixture was filtered. The filtrate was concentrated and recrystallized from ethanol-ether, giving 4.71 g of 2{4-(2-hydroxy-3-methoxypropoxy)-phenylcarbamoyl}ethyldimethylsulfonium p-toluenesulfonate (Compound 7) in 96.9% yield, M.P. 144° to 146° C.

EXAMPLE 13

Using suitable starting materials, the procedure of Example 12 was repeated, producing Compounds 20, 23, 30, 31, 33 and 39 as shown in Table 1 to be given later.

EXAMPLE 14

Synthesis of 2-{3-(2-phenoxycarbonyloxy-3-ethoxypropoxy)phenylcarbamoyl}ethyldimethylsulfonium p-toluenesulfonate (Compound 24)

Dissolved in 10 ml of acetonitrile was 4.34 g of 2-{3-(2-phenoxycarbonyloxy-3-ethoxypropoxy)phenylcarbamoyl}ethyl methyl sulfide. To the solution were added 5.00 g of propyl iodide and subsequently 2.79 g of silver p-toluenesulfonate. The mixture was stirred at room temperature for 12 hours. The reaction mixture was filtered and the same subsequent procedure as in Example 12 was followed to give 6.05 g of 2-{3-(2-phenoxycarbonyloxy-3-ethoxypropoxy)phenylcarbamoyl}ethyldimethylsulfonium p-toluenesulfonate (Compound 24) in 93.4% yield.

REFERENCE EXAMPLE 3

Synthesis of 2-{4-(2,3-dihydroxypropoxy)phenoxy}ethyl methyl sulfide

A 1.84 g quantity of 4-(2,3-dihydroxypropoxy)phenol was dissolved in 0.40 g of sodium hydroxide and 10 ml of 90% methanol. To the solution was added 1.11 g of 2-methylmercaptoacetyl chloride, and the mixture was refluxed for 6 hours. The reaction mixture was concentrated and the residue was extracted with chloroform. The chloroform layer was washed with water, dewatered with Glauber's salt and concentrated. The residue was recrystallized from benzene-petroleum ether, giving 2.25 g of 2-{4-(2,3-dihydroxypropoxy)phenoxy}ethyl methyl sulfide in 87.2% yield, M.P. 59° to 61° C.

| Elementary analysis (for $C_{12}H_{18}O_4S$) | | |
|---|---|---|
| | C | H |
| Calcd. (%) | 55.79 | 7.02 |
| Found (%) | 55.61 | 7.18 |

REFERENCE EXAMPLE 4

Synthesis of 2-{4-(2,3-diethoxypropoxy)phenoxy}ethyl methyl sulfide

A 2.40 g quantity of 4-(2,3-diethoxypropoxy)phenol was dissolved in 0.56 g of potassium hydroxide and 10 ml of 90% ethanol. To the solution was added 1.55 g of 2-methylmercaptoethyl bromide. The mixture was stirred at room temperature for 12 hours. The reaction mixture was concentrated and the residue was extracted with chloroform. The chloroform layer was washed with water, dewatered with Glauber's salt and concentrated. The residue was distilled at reduced pressure, giving 2.95 g of 2-{4-(2,3-diethoxypropoxy)phenoxy}ethyl methyl sulfide in 93.9% yield, b.p. 176° to 177° C./1 to 2 mmHg.

EXAMPLE 15

Synthesis of
2-{2-(2,3-dihydroxypropoxy)phenoxy}ethyldimethyl-
sulfonium p-toluenesulfonate (Compound 40)

A 7 g quantity of methyl p-toluenesulfonate was added to 2.58 g of 2-{2-(2,3-dihydroxypropoxy)phenoxy}ethyl methyl sulfide and 5 ml of methylene chloride and the mixture was stirred at room temperature for 24 hours. Ether was added to the reaction mixture. The oily product precipitated was separated and purified with ethanol-ether, affording 4.01 g of 2-{2-(2,3-dihydroxypropoxy)phenoxy}ethyldimethylsulfonium p-toluenesulfonate in 90.1% yield.

EXAMPLE 16

Using suitable starting materials, the procedure of Example 15 was repeated to produce Compounds 42, 44, 48 and 54 as shown in Table 1 to be given later.

EXAMPLE 17

Synthesis of
2-{4-(2-hydroxy-3-methoxypropoxy)phenoxy}ethyl-
dimethylsulfonium p-toluenesulfonate (Compound 45)

A 6 g quantity of methyl p-toluenesulfonate was added to 2.72 g of 2-{4-(2-hydroxy-3-methoxypropoxy)phenoxy}ethyl methyl sulfide. The mixture was stirred at room temperature for 12 hours. Ether was added to the reaction mixture and the insoluble solid was separated and recrystallized from ethanol-ether, giving 4.15 g of 2-{4-(2-hydroxy-3-methoxypropoxy)phenoxy}ethyldimethylsulfonium p-toluenesulfonate in 90.4% yield, M.P. 88° to 91° C.

EXAMPLE 18

Using suitable starting materials, the procedure of Example 17 was repeated, producing Compounds 46, 47, 49, 52, 55 and 56 as shown in Table 1 to be given later.

EXAMPLE 19

Synthesis of
2-{4-(2-hydroxy-3-phenoxypropoxy)phenoxy}ethyl-
dimethylsulfonium iodide (Compound 50)

A 5 g quantity of methyl iodide was added to 3.34 g of 2-{4-(2-hydroxy-3-phenoxypropoxy)phenoxy}ethyl methyl sulfide and 5 ml of acetonitrile. The mixture was stirred at room temperature for 24 hours. The reaction mixture was concentrated and the residue was recrystallized from ethanol-ether, giving 4.45 g of 2-{4-(2-hydroxy-3-phenoxypropoxy)phenoxy}ethyldimethylsulfonium iodide in 93.5% yield, M.P. 112° to 112.8° C.

EXAMPLE 20

Using suitable starting materials, the procedure of Example 19 was repeated, producing Compounds 59 as shown in Table 1 to be given later.

EXAMPLE 21

Synthesis of
3-{4-(3-ethoxy-2-hydroxypropoxy)phenoxy}propyl-
dimethylsulfonium p-toluenesulfonate (Compound 60)

Dissolved in 20 ml of acetonitrile was 4.42 g of 3-{4-(3-ethoxy-2-hydroxypropoxy)phenoxy}propyldimethylsulfonium iodide produced in Example 20. A 2.79 g quantity of silver p-toluenesulfonate was added to the solution. The mixture was stirred at room temperature for 1 hour. The reaction mixture was filtered and hydrogen sulfide and active carbon were added to the filtrate. The mixture was filtered and the filtrate was concentrated. The residue was recrystallized from ethanol-ether, giving 4.48 g of 3-{4-(3-ethoxy-2-hydroxypropoxy)phenoxy}-propyldimethylsulfonium p-toluenesulfonate in 92.0% yield, M.P. 114° to 116° C.

EXAMPLE 22

Synthesis of
2-{4-(2,3-dipropoxypropoxy)phenoxy}ethyldimethyl-
sulfonium p-toluenesulfonate (Compound 53)

A 5 g quantity of methyl iodide and then 2.79 g of silver p-toluenesulfonate were added to 3.42 g of 2-{4-(2,3-dipropoxypropoxy)phenoxy}ethyl methyl sulfide and 20 ml of acetonitrile. The mixture was stirred at room temperature for 12 hours. The reaction mixture was filtered and hydrogen sulfide and active carbon were added to the filtrate. The mixture was filtered and the filtrate was concentrated. The residue was recrystallized from methanol-isopropyl ether, giving 4.81 g of 2-{4-(2,3-dipropoxypropoxy)phenoxy}ethyldimethylsulfonium p-toluenesulfonate in 90.9% yield, M.P. 123° to 125° C.

EXAMPLE 23

Using suitable starting materials, the procedure of Example 22 was repeated, producing Compounds 57 and 58 as shown in Table 1 to be given later.

EXAMPLE 24

Synthesis of
2-{4-(2-hydroxy-3-phenoxypropoxy)phenoxy}ethyl-
dimethylsulfonium p-toluenesulfonate (Compound 51)

Dissolved in 20 ml of acetonitrile was 4.76 g of 2-{4-(2-hydroxy-3-phenoxypropoxy)phenoxy}ethyl dimethylsulfonium iodide produced in Example 19. A 2.32 g quantity of silver oxide was added to the solution and the mixture was stirred for 30 minutes. The reaction mixture was filtered and 3.44 g of p-toluenesulfonic acid was added to the filtrate. The mixture was concentrated. The residue was recrystallized from acetonitrile-ether, giving 4.65 g of 2-{4-(2-hydroxy-3-phenoxypropoxy)phenoxy}ethyldimethylsulfonium p-toluenesulfonate in 89.3% yield, M.P. 88° to 90° C.

EXAMPLE 25

Synthesis of
2-{2-(2,3-dihydroxypropoxy)phenoxy}ethyldimethyl-
sulfonium picrylsulfonate (Compound 41)

Dissolved in 2 ml of water was 4.45 g of 2-{2-(2,3-dihydroxypropoxy)phenoxy}ethyldimethylsulfonium p-toluenesulfonate. To the solution was added a solution of 6.30 g of sodium picrylsulfonate in 10 ml of water. The crystals formed were filtered off and recrystallized from ethanol, giving 5.10 g of 2-{2-(2,3-dihydroxypropoxy)phenoxy}ethyldimethylsulfonium picrylsulfonate in 90.1%, M.P. 124° to 125° C.

EXAMPLE 26

Using suitable starting materials, the procedure of Example 25 was repeated, producing Compound 43 as shown in Table 1 to be given later.

EXAMPLE 27

Synthesis of 3-{3-(3-ethoxy-2-propionyloxypropoxy)phenoxy} propylmethyl propylsulfonium p-toluenesulfonate (Compound 61)

Dissolved in 20 ml of methylene chloride was 3.56 g of 3-{3-(3-ethoxy-2-propionyloxypropoxy)phenoxy} propyl methyl sulfide. To the solution were added 5 g of methyl iodide and 2.79 g of silver p-toluenesulfonate and the mixture was stirred at room temperature for 24 hours. The reaction mixture was filtered. Hydrogen sulfide and active carbon were added to the filtrate, and the mixture was subsequently filtered. The resulting filtrate was concentrated and the residue was purified by acetonitrile-isopropyl ether, giving 4.95 g of 3-{3-(3-ethoxy-2-propionyloxypropoxy)phenoxy}propylmethylpropylsulfonium p-toluenesulfonate in 91.2% yield.

REFERENCE EXAMPLE 5

Synthesis of 2-{4-(3-ethoxy-2-methoxyacetoxypropoxy)phenylcarbamoyl}ethyl methyl sulfide Dissolved in 60 ml of benzene were 3.13 g of 2-{4-(3-ethoxy-2-hydroxypropoxy)carbamoyl}ethyl methyl sulfide and 0.87 g of pyridine. To the solution was added dropwise 1.09 g of methoxy-acetyl chloride with ice-cooling. The mixture was stirred at room temperature for 3 hours and the reaction mixture was washed with water and concentrated. The residue was purified by silica gel column chromatography using a 2:5 acetonebenzene mixture, giving 3.50 g of 2-{4-(3-ethoxy-2-methoxyacetoxypropoxy)phenylcarbamoyl}ethyl methyl sulfide in 90.9% yield.

NMR (DMSO-$d_6$, δ value, ppm): 1.10 (3H, C$\underline{H}_3$CH$_2$O—), 2.09 (3H, C$\underline{H}_3$S—), 2.4–2.9 (4H, CH$_3$SC$\underline{H}_2$C$\underline{H}_2$CONH—), 3.37 (3H, C$\underline{H}_3$O—), 3.47 (2H, CH$_3$C$\underline{H}_2$O—), 3.62

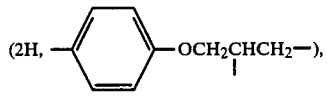

4.06 (2H, CH$_3$OC$\underline{H}_2$CO), 4.09

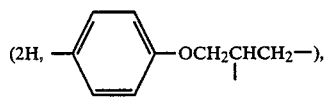

5.1–5.4

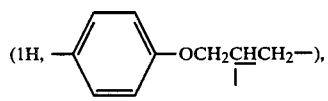

6.88, 7.51

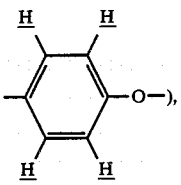

9.85 (1H, CONH).

REFERENCE EXAMPLE 6

Synthesis of 2-{2-(3-butoxy-2-phenoxyacetoxypropoxy)phenylcarbamoyl}ethyl propyl sulfide Dissolved in 100 ml of chloroform were 3.70 g of 2-{2-(3-butoxy-2-hydroxypropoxy)phenylcarbamoyl}ethyl propyl sulfide and 0.87 g of pyridine. To the solution was added dropwise 1.71 g of phenoxyacetyl chloride. The mixture was stirred at room temperature for 2 hours and the reaction mixture was washed with water and concentrated. The residue was purified by silica gel column chromatography using a 5:3 ether-petroleum ether mixture, giving 4.80 g of 2-{2-(3-butoxy-2-phenoxyacetoxypropoxy)phenylcarbamoyl}ethyl propyl sulfide in 95.2% yield.

NMR (DMSO-$d_6$, δ value, ppm): 0.87 (3H, C$\underline{H}_3$CH$_2$CH$_2$CH$_2$O—), 0.91 (3H, C$\underline{H}_3$CH$_2$CH$_2$S—), 1.0–1.7 (6H, CH$_3$C$\underline{H}_2$C$\underline{H}_2$S—, CH$_3$C$\underline{H}_2$C$\underline{H}_2$CH$_2$O—), 2.3–2.6 (2H, CH$_3$CH$_2$C$\underline{H}_2$S—), 2.5–2.8 (4H, SC$\underline{H}_2$C$\underline{H}_2$CONH—), 3.2–3.6 (2H, CH$_3$CH$_2$CH$_2$C$\underline{H}_2$O—), 3.68

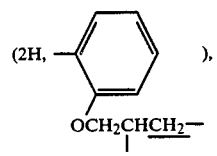

4.0–4.3

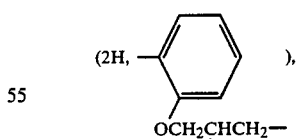

4.81

5.3–5.6

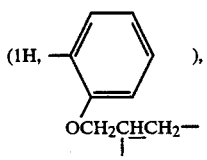

(1H, ), 6.7–7.4

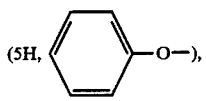

(5H, ), 6.7–7.2, 7.9–8.1

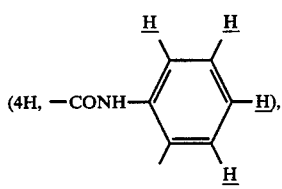

(4H, —CONH— —H), 8.7 (1H, CONH).

EXAMPLE 28

Synthesis of 2-{4-(3-ethoxy-2-methoxyacetoxypropoxy)phenylcarbamoyl}ethyldimethylsulfonium p-toluenesulfonate (Compound 62)

Dissolved in 30 ml of methylene chloride was 3.85 g of 2-{4-(3-ethoxy-2-methoxyacetoxypropoxy)phenylcarbamoyl}ethyl methyl sulfide. Thereto was added 5.58 g of methyl p-toluenesulfonate and the mixture was stirred at room temperature for 48 hours. Isopropyl ether was adde to the reaction mixture and the insoluble solid was separated. The solid was purified with acetonitrile-ether, giving 5.30 g of 2-{4-(3-ethoxy-2-methoxyacetoxypropoxy)phenylcarbamoyl}ethyldimethylsulfonium p-toluenesulfonate (Compound 62) in 92.7% yield.

EXAMPLE 29

Synthesis of 2-{3-(2-acetylacetyloxy-3-propylcarbamoyloxypropoxy)phenylcarbamoyl}ethyldimethylsulfonium p-toluenesulfonate (Compound 72)

A 5.5 g quantity of methyl p-toluenesulfonate was added to 4.54 g of 2-{3-(2-acetylacetyloxy-3-propylcarbamoyloxypropoxy)phenylcarbamoyl}ethyl methyl sulfide. The mixture was stirred at room temperature for 24 hours. Ether was added to the reaction mixture. The insoluble solid was filtered off, and was recrystallized from acetonitrile-ether, giving 6.10 g of 2-{3-(2-acetylacetyloxy-3-propylcarbamoyloxypropoxy)phenylcarbamoyl}ethyldimethylsulfonium p-toluenesulfonate in 95.2% yield, M.P. 74° to 76° C.

EXAMPLE 30

Synthesis of 2-{3-(2-acetylaminoacetoxy-3-methoxypropoxy)phenylcarbamoyl}ethylbutylmethylsulfonium iodide (Compound 63)

Dissolved in 4 ml of dimethylformamide was 4.41 g of 2-{3-(2-acetylaminoacetoxy-3-methoxypropoxy)phenylcarbamoyl}ethyl butyl sulfide. Thereto was added 5.00 g of methyl iodide and the mixture was stirred at room temperature for 24 hours. Ether was added to the reaction mixture and the insoluble solid was separated. The solid was purified with ethanol-ether, giving 5.20 g of 2-{3-(2-acetylaminoacetoxy-3-methoxypropoxy)phenyl carbamoyl}ethylbutylmethylsulfonium iodide (Compound 63) in 89.3% yield.

EXAMPLE 31

Using suitable starting materials, the procedure of Example 30 was repeated, producing Compounds 65 and 71 as shown in Table 1 to be given later.

EXAMPLE 32

Synthesis of 2-{2-(3-butoxy-2-phenoxyacetoxypropoxy)phenylcarbamoyl}ethyldipropylsulfonium p-toluenesulfonate (Compound 66)

A 5.10 g quantity of propyl iodide and then 2.79 g of silver p-toluenesulfonate were added to 5.04 g of 2-{2-(3-butoxy-2-phenoxyacetoxypropoxy)phenylcarbamoyl}ethyl propyl sulfide and 20 ml of acetonitrile. The mixture was stirred at room temperature for 12 hours. The reaction mixture was filtered and hydrogen sulfide and active carbon were added to the filtrate. The mixture was filtered and the filtrate was concentrated. The residue was purified with acetonitrile-isopropyl ether, giving 6.80 g of 2-{2-(3-butoxy-2-phenoxyacetoxypropoxy)phenylcarbamoyl}ethyldipropylsulfonium p-toluenesulfonate (Compound 66) in 94.7% yield.

EXAMPLE 33

Using suitable starting materials, the procedure of Example 32 was repeated, producing Compounds 67, 68, 69 and 70 as shown in Table 1 to be given later.

EXAMPLE 34

Synthesis of 2-{3-(2-acetylaminoacetoxy-3-methoxypropoxy)phenylcarbamoyl}ethylbutylmethylsulfonium p-toluenesulfonate (Compound 64)

Dissolved in 50 ml of acetonitrile was 5.82 g of 2-{3-(2-acetylaminoacetoxy-3-methoxypropoxy)phenylcarbamoyl}ethylbutylmethylsulfonium iodide produced in Example 30. Thereto was added 2.31 g of silver oxide. The mixture was stirred at room temperature for 30 minutes and filtered. To the filtrate was added a solution of 3.44 g of p-toluenesulfonic acid in 20 ml of acetonitrile. The mixture was concentrated. The residue was recrystallized from acetonitrile-isopropyl ether, affording 5.80 g of 2-{3-(2-acetylaminoacetoxy-3-methoxypropoxy)phenylcarbamoyl}ethylbutylmethylsulfonium p-toluenesulfonate (Compound 64) in 92.5% yield.

Table 1 given below shows the structures of the compounds (Compounds 1 to 77) obtained in the foregoing Examples and Table 1 below indicates the yields and melting points of the compounds produced in the Examples, and the results of analysis by nuclear magnetic resonance (NMR) (δ value, ppm) or the elementary analysis. NMR values are those determined in DMSO-d$_6$ using TMS as an internal standard. The parenthesized values and the values without parenthesis in the elementary analysis data represent those as calculated (%) and those as found (%), respectively.

TABLE 1

| Comp. No. | Compound |
|---|---|
| 1 | CH$_3$\\$\overset{\oplus}{S}$CH$_2$CONH—⟨C$_6$H$_4$⟩—OCH$_2$CHCH$_2$OCH$_2$CH$_3$ / CH$_3$ ; OH ; CH$_3$—⟨C$_6$H$_4$⟩—SO$_3^\ominus$ |
| 2 | CH$_3$\\$\overset{\oplus}{S}$CH$_2$CONH—⟨C$_6$H$_4$⟩—OCH$_2$CHCH$_2$OCH$_2$CH$_3$ / CH$_3$ ; OCOCH$_3$ ; CH$_3$—⟨C$_6$H$_4$⟩—SO$_3^\ominus$ |
| 3 | CH$_3$\\$\overset{\oplus}{S}$CH$_2$CH$_2$CONH—⟨C$_6$H$_4$⟩—OCH$_2$CHCH$_2$OH / CH$_3$ ; OH ; I$^\ominus$ |
| 4 | CH$_3$\\$\overset{\oplus}{S}$CH$_2$CH$_2$CONH—⟨C$_6$H$_4$⟩—OCH$_2$CHCH$_2$OH / CH$_3$ ; OH ; CH$_3$—⟨C$_6$H$_4$⟩—SO$_3^\ominus$ |
| 5 | CH$_3$\\$\overset{\oplus}{S}$CH$_2$CH$_2$CONH—⟨C$_6$H$_4$⟩—OCH$_2$CH$_2$CH$_2$OH / CH$_3$ ; CH$_3$—⟨C$_6$H$_4$⟩—SO$_3^\ominus$ |
| 6 | CH$_3$\\$\overset{\oplus}{S}$CH$_2$CH$_2$CONH—⟨C$_6$H$_4$⟩—OCH$_2$CHCH$_3$ / CH$_3$ ; OH ; CH$_3$—⟨C$_6$H$_4$⟩—SO$_3^\ominus$ |
| 7 | CH$_3$\\$\overset{\oplus}{S}$CH$_2$CH$_2$CONH—⟨C$_6$H$_4$⟩—OCH$_2$CHCH$_2$OCH$_3$ / CH$_3$ ; OH ; CH$_3$—⟨C$_6$H$_4$⟩—SO$_3^\ominus$ |
| 8 | CH$_3$\\$\overset{\oplus}{S}$CH$_2$CH$_2$CONH—⟨C$_6$H$_4$⟩—OCH$_2$CHCH$_2$OCH$_2$CH$_3$ / CH$_3$ ; OH ; CH$_3$—⟨C$_6$H$_4$⟩—SO$_3^\ominus$ |
| 9 | CH$_3$\\$\overset{\oplus}{S}$CH$_2$CH$_2$CONH—⟨C$_6$H$_4$⟩—OCH$_2$CHCH$_2$OCH$_2$CH$_2$CH$_3$ / CH$_3$ ; OH ; I$^\ominus$ |
| 10 | CH$_3$\\$\overset{\oplus}{S}$CH$_2$CH$_2$CONH—⟨C$_6$H$_4$⟩—OCH$_2$CHCH$_2$OCH$_2$CH$_2$CH$_3$ / CH$_3$ ; OH ; CH$_3$—⟨C$_6$H$_4$⟩—SO$_3^\ominus$ |
| 11 | CH$_3$\\$\overset{\oplus}{S}$CH$_2$CH$_2$CONH—⟨C$_6$H$_4$⟩—OCH$_2$CHCH$_2$OCH$_2$CH$_2$CH$_3$ / CH$_3$ ; OH ; 2,4,6-(NO$_2$)$_3$C$_6$H$_2$SO$_3^\ominus$ |
| 12 | CH$_3$\\$\overset{\oplus}{S}$CH$_2$CH$_2$CONH—⟨C$_6$H$_4$⟩—OCH$_2$CHCH$_2$OCH(CH$_3$)$_2$ / CH$_3$ ; OH ; CH$_3$—⟨C$_6$H$_4$⟩—SO$_3^\ominus$ |
| 13 | CH$_3$\\$\overset{\oplus}{S}$CH$_2$CH$_2$CONH—⟨C$_6$H$_4$⟩—OCH$_2$CHCH$_2$O(CH$_2$)$_3$CH$_3$ / CH$_3$ ; OH ; I$^\ominus$ |
| 14 | CH$_3$\\$\overset{\oplus}{S}$CH$_2$CH$_2$CONH—⟨C$_6$H$_4$⟩—OCH$_2$CHCH$_2$O(CH$_2$)$_3$CH$_3$ / CH$_3$ ; OH ; CH$_3$—⟨C$_6$H$_4$⟩—SO$_3^\ominus$ |

TABLE 1-continued
| Comp. No. | Compound | Comp. No. | Compound |
|---|---|---|---|
| 15 | 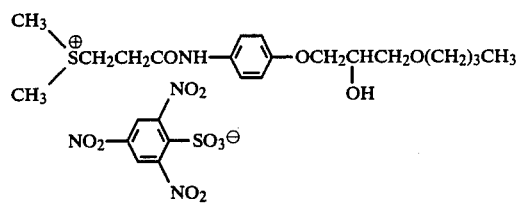 | 16 | 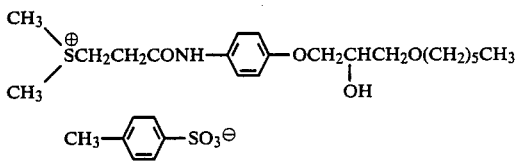 |
| 17 | 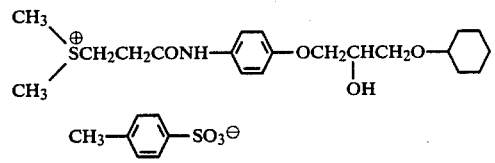 | 18 | 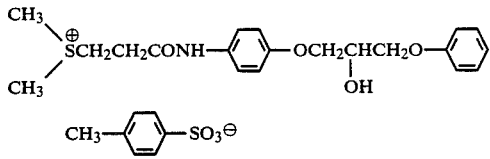 |
| 19 | 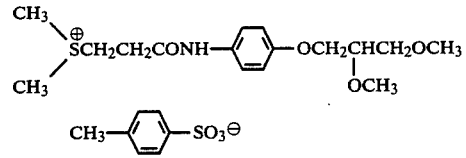 | 20 | 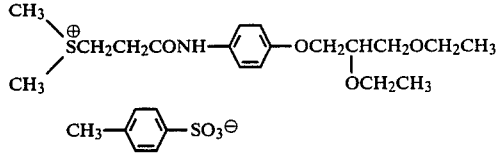 |
| 21 | 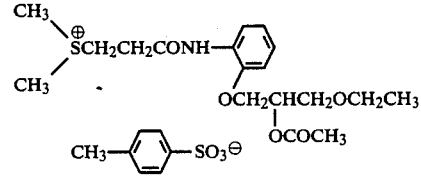 | 22 | 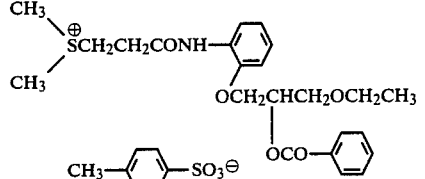 |
| 23 | 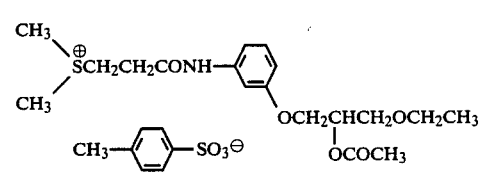 | 24 | 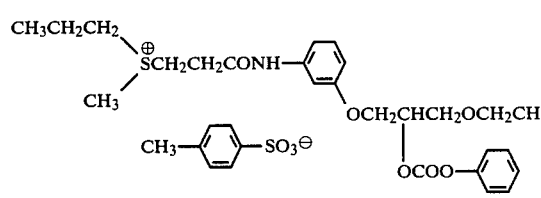 |
| 25 | 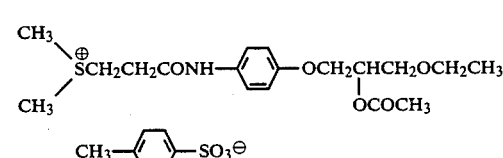 | 26 | 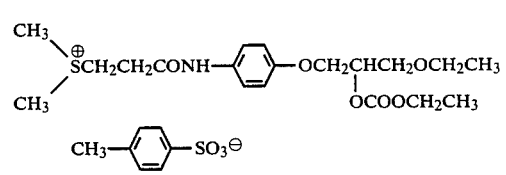 |
| 27 | 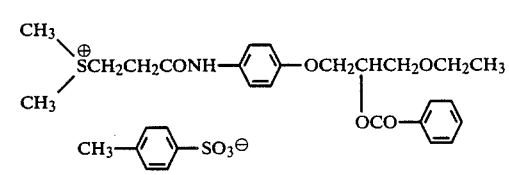 | 28 | 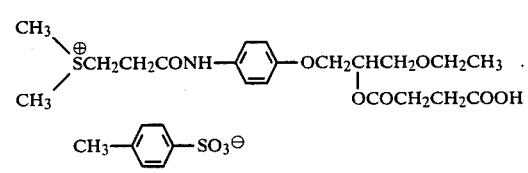 |

TABLE 1-continued

| Comp. No. | Compound |
|---|---|
| 29 | (CH₃)₂S⁺CH₂CH₂CONH—C₆H₄—OCH₂CH(OCH₂CH₃)CH₂OCH₂CH₃ · CH₃C₆H₄SO₃⁻ |
| 30 | (CH₃)₂S⁺CH₂CH₂CONH—C₆H₄—OCH₂CH(O(CH₂)₃CH₃)CH₂O(CH₂)₃CH₃ · CH₃C₆H₄SO₃⁻ |
| 31 | (CH₃)₂S⁺CH₂CH₂CONH—C₆H₄—OCH₂CH(O(CH₂)₅CH₃)CH₂O(CH₂)₅CH₃ · CH₃C₆H₄SO₃⁻ |
| 32 | (CH₃)₂S⁺CH₂CH₂CONH—C₆H₄—OCH₂CH(OCOCH₃)CH₂OCOCH₃ · CH₃C₆H₄SO₃⁻ |
| 33 | (CH₃)₂S⁺CH₂CH₂CONH—C₆H₄—OCH₂CH(OCOC(CH₃)₃)CH₂OCOC(CH₃)₃ · CH₃C₆H₄SO₃⁻ |
| 34 | (CH₃)₂S⁺CH₂CH₂CONH—C₆H₄—OCH₂CH(OCOC₆H₅)CH₂OCOC₆H₅ · CH₃C₆H₄SO₃⁻ |
| 35 | (CH₃CH₂)₂S⁺CH₂CH₂CH₂CONH—C₆H₄—OCH₂CH(OCOOCH₂CH₃)CH₂OCH₂CH₃ · I⁻ |
| 36 | (CH₃CH₂)₂S⁺CH₂CH₂CH₂CONH—C₆H₄—OCH₂CH(OCOOCH₂CH₃)CH₂OCH₂CH₃ · CH₃C₆H₄SO₃⁻ |
| 37 | (CH₃)(CH₃CH₂)S⁺CH₂CH₂CH₂CONH—C₆H₄—OCH₂CH(OCOCH₂CH₃)CH₂OCH₂CH₃ · I⁻ |
| 38 | (CH₃)(CH₃CH₂)S⁺CH₂CH₂CH₂CONH—C₆H₄—OCH₂CH(OCOCH₂CH₃)CH₂OCH₂CH₃ · CH₃C₆H₄SO₃⁻ |
| 39 | (CH₃)₂S⁺CH₂CH₂CH₂CONH—C₆H₄—OCH₂CH(OCOCH₃)CH₂OCH₂CH₃ · CH₃C₆H₄SO₃⁻ |
| 40 | (CH₃)₂S⁺CH₂CH₂O—C₆H₄—OCH₂CH(OH)CH₂OH · CH₃C₆H₄SO₃⁻ |
| 41 | (CH₃)₂S⁺CH₂CH₂O—C₆H₄—OCH₂CH(OH)CH₂OH · 2,4,6-(NO₂)₃C₆H₂SO₃⁻ |
| 42 | (CH₃)₂S⁺CH₂CH₂O—C₆H₄—OCH₂CH(OH)CH₂OH · CH₃C₆H₄SO₃⁻ |

TABLE 1-continued

| Comp. No. | Compound |
|---|---|
| 43 | (CH₃)₂S⁺CH₂CH₂O—C₆H₄—OCH₂CH(OH)CH₂OH ; 2,4,6-trinitrobenzenesulfonate⁻ |
| 44 | (CH₃)₂S⁺CH₂CH₂O—C₆H₄—OCH₂CH(OH)CH₂OH ; CH₃-C₆H₄-SO₃⁻ |
| 45 | (CH₃)₂S⁺CH₂CH₂O—C₆H₄—OCH₂CH(OH)CH₂OCH₃ ; CH₃-C₆H₄-SO₃⁻ |
| 46 | (CH₃)₂S⁺CH₂CH₂O—C₆H₄—OCH₂CH(OH)CH₂OCH₂CH₃ ; CH₃-C₆H₄-SO₃⁻ |
| 47 | (CH₃)₂S⁺CH₂CH₂O—C₆H₄—OCH₂CH(OH)CH₂OCH₂CH₂CH₃ ; CH₃-C₆H₄-SO₃⁻ |
| 48 | (CH₃)₂S⁺CH₂CH₂O—C₆H₄—OCH₂CH(OH)CH₂OCH₂CH₂OCH₂CH₃ ; CH₃-C₆H₄-SO₃⁻ |
| 49 | (CH₃)₂S⁺CH₂CH₂O—C₆H₄—OCH₂CH(OH)CH₂OCH₂-(tetrahydrofuran-2-yl) ; CH₃-C₆H₄-SO₃⁻ |
| 50 | (CH₃)₂S⁺CH₂CH₂O—C₆H₄—OCH₂CH(OH)CH₂O—C₆H₅ ; I⁻ |
| 51 | (CH₃)₂S⁺CH₂CH₂O—C₆H₄—OCH₂CH(OH)CH₂O—C₆H₅ ; CH₃-C₆H₄-SO₃⁻ |
| 52 | (CH₃)₂S⁺CH₂CH₂O—C₆H₄—OCH₂CH(OCH₂CH₃)CH₂OCH₂CH₃ ; CH₃-C₆H₄-SO₃⁻ |
| 53 | (CH₃)₂S⁺CH₂CH₂O—C₆H₄—OCH₂CH(OCH₂CH₃)CH₂OCH₂CH₂CH₃ ; CH₃-C₆H₄-SO₃⁻ |
| 54 | (CH₃)₂S⁺CH₂CH₂O—C₆H₄—OCH₂CH(OH)CH₂OCONH₂ ; CH₃-C₆H₄-SO₃⁻ |
| 55 | (CH₃)₂S⁺CH₂CH₂O—C₆H₄—OCH₂CH(OCOCH₃)CH₂OCOCH₃ ; CH₃-C₆H₄-SO₃⁻ |
| 56 | (CH₃)₂S⁺CH₂CH₂O—C₆H₄—OCH₂CH(OCOC₆H₅)CH₂OCOC₆H₅ ; CH₃-C₆H₄-SO₃⁻ |

TABLE 1-continued

| Comp. No. | Compound |
|---|---|
| 57 | (CH₃)₂S⁺CH₂CH₂O—C₆H₄—OCH₂CH₂CH₂OH · CH₃-C₆H₄-SO₃⁻ |
| 58 | (CH₃)₂S⁺CH₂CH₂O—C₆H₄—OCH₂CH(OH)CH₃ · CH₃-C₆H₄-SO₃⁻ |
| 59 | (CH₃)₂S⁺CH₂CH₂CH₂O—C₆H₄—OCH₂CH(OH)CH₂OCH₂CH₃ · I⁻ |
| 60 | (CH₃)₂S⁺CH₂CH₂CH₂O—C₆H₄—OCH₂CH(OH)CH₂OCH₂CH₃ · CH₃-C₆H₄-SO₃⁻ |
| 61 | (CH₃CH₂CH₂)(CH₃)S⁺CH₂CH₂CH₂O—C₆H₄—OCH₂CH(OCOCH₂CH₃)CH₂OCH₂CH₃ · CH₃-C₆H₄-SO₃⁻ |
| 62 | (CH₃)₂S⁺CH₂CH₂CONH—C₆H₄—OCH₂CH(OCOCH₂OCH₃)CH₂OCH₂CH₃ · CH₃-C₆H₄-SO₃⁻ |
| 63 | (CH₃)(CH₃CH₂CH₂CH₂)S⁺CH₂CH₂CONH—C₆H₄—OCH₂CH(OCOCH₂NHCOCH₃)CH₂OCH₃ · I⁻ |
| 64 | (CH₃)(CH₃CH₂CH₂CH₂)S⁺CH₂CH₂CONH—C₆H₄—OCH₂CH(OCOCH₂NHCOCH₃)CH₂OCH₃ · CH₃-C₆H₄-SO₃⁻ |
| 65 | (CH₃CH₂CH₂)₂S⁺CH₂CH₂CONH—C₆H₄—OCH₂CH(OCOCH₂-O-C₆H₅)CH₂OCH₂CH₂CH₂CH₃ · I⁻ |
| 66 | (CH₃CH₂CH₂)₂S⁺CH₂CH₂CONH—C₆H₄—OCH₂CH(OCOCH₂-O-C₆H₅)CH₂OCH₂CH₂CH₂CH₃ · CH₃-C₆H₄-SO₃⁻ |
| 67 | (CH₃CH₂CH₂)(CH₃)S⁺CH₂CH₂CH₂CONH—C₆H₄—OCH₂CH(OCOOCH₂-C₆H₅)CH₂OCOOCH₂-C₆H₅ · CH₃-C₆H₄-SO₃⁻ |
| 68 | (CH₃)(CH₃CH₂)S⁺CH₂CH₂CONH—C₆H₄—OCH₂CH(OCOOCH₂CH(CH₃)₂)CH₂OCOOCH₂CH(CH₃)₂ · CH₃-C₆H₄-SO₃⁻ |

TABLE 1-continued

| Comp. No. | Compound |
|---|---|
| 69 | CH₃CH₂\\S⁺(CH₃CH₂)CH₂CH₂CH₂CONH—⟨C₆H₄⟩—OCH₂CH(OCOCH(OH)CH₃)CH₂OCONH—⟨C₆H₅⟩   CH₃—⟨C₆H₄⟩—SO₃⁻ |
| 70 | CH₃CH₂\\S⁺(CH₃CH₂)CH₂CH₂CH₂CONH—⟨C₆H₄⟩—OCH₂CH(OCH₂—⟨C₆H₅⟩)CH₂OCH₂CH₃   CH₃—⟨C₆H₄⟩—SO₃⁻ |
| 71 | CH₃\\S⁺(CH₃CH₂CH₂CH₂)CH₂CH₂CH₂CONH—⟨C₆H₄⟩—OCH₂CH(OCH₂OCH₂—⟨C₆H₅⟩)CH₂O—⟨C₆H₅⟩   I⁻ |
| 72 | CH₃\\S⁺(CH₃)CH₂CH₂CONH—⟨C₆H₄⟩—OCH₂CH(OCOCH₂COCH₃)CH₂OCONHCH₂CH₂CH₃   CH₃—⟨C₆H₄⟩—SO₃⁻ |
| 73 | CH₃\\S⁺(CH₃)CH₂CH₂CONH—⟨C₆H₄⟩—OCH₂CH(OC₂H₅)CH₂OCOCH₃   CH₃—⟨C₆H₄⟩—SO₃⁻ |
| 74 | CH₃\\S⁺(CH₃)CH₂CH₂CONH—⟨C₆H₄⟩—OCH₂CH(OC₂H₅)CH₂OH   CH₃—⟨C₆H₄⟩—SO₃⁻ |
| 75 | CH₃CH₂CH₂CH₂\\S⁺(CH₃)CH₂CH₂CH₂CONH—⟨C₆H₄⟩—OCH₂CH(OH)CH₂O—⟨C₆H₅⟩   I⁻ |
| 76 | (CH₃CH₂CH₂)₂S⁺CH₂CH₂CONH—⟨C₆H₄⟩—OCH₂CH(OH)CH₂OCH₂CH₂CH₃   I⁻ |
| 77 | (CH₃CH₂CH₂)₂S⁺CH₂CH₂CONH—⟨C₆H₄⟩—OCH₂CH(OH)CH₂OCH₂CH₂CH₃   CH₃—⟨C₆H₄⟩—SO₃⁻ |

TABLE 2

| Comp. No. | m.p. (°C.) | Yield (%) | Elementary analysis or NMR | | |
|---|---|---|---|---|---|
| | | | For $C_{22}H_{31}NO_7S_2$ | | |
| | | | C | H | N |
| 1 | 139–141 | 97.7 | (54.41) | (6.43) | (2.88) |
| | | | 54.31 | 6.40 | 2.75 |
| | | | For $C_{24}H_{33}NO_8S_2$ | | |
| | | | C | H | N |
| 2 | 100–105 | 96.6 | (54.63) | (6.30) | (2.65) |
| | | | 54.35 | 6.25 | 2.51 |
| | | | For $C_{14}H_{22}NO_4SI$ | | |
| | | | C | H | N |
| 3 | 113–115 | 94.8 | (39.35) | (5.19) | (3.28) |
| | | | 39.31 | 5.33 | 3.43 |

TABLE 2-continued

| Comp. No. | m.p. (°C.) | Yield (%) | Elementary analysis or NMR |
|---|---|---|---|
| 4 | | 96.3 | 2.28 (3H, CH₃—C₆H₄—SO₃), 2.93 (6H, (CH₃)₂S—), 3.7–4.1 (3H, —C₆H₄—OCH₂CH—), 6.90, 7.50 (4H, C₆H₄—O—), 7.12, 7.53 (4H, CH₃—C₆H₄—SO₃), 10.15 (1H, CONH) |
| 5 | | 90.7 | 2.28 (3H, CH₃—C₆H₄—SO₃), 2.93 (6H, (CH₃)₂S—), 6.88, 7.50 (4H, C₆H₄—O—), 7.10, 7.50 (4H, CH₃—C₆H₄—SO₃), 10.11 (1H, CONH) |
| 6 | | 91.5 | 1.14 (3H, CH₃CH—OH), 2.28 (3H, CH₃—C₆H₄—SO₃), 2.93 (6H, (CH₃)₂S—), 6.90, 7.45 (4H, C₆H₄—O—), 7.10, 7.49 (4H, CH₃—C₆H₄—SO₃), 10.11 (1H, CONH) |

| Comp. No. | m.p. (°C.) | Yield (%) | | | |
|---|---|---|---|---|---|
| | | | For C₂₂H₃₁NO₇S₂ | | |
| | | | C | H | N |
| 7 | 144–146 | 96.9 | (54.41) 54.30 | (6.43) 6.39 | (2.88) 2.71 |
| | | | For C₂₃H₃₃NO₇S₂ | | |
| | | | C | H | N |
| 8 | 70–73 | 91.3 | (55.29) 55.10 | (6.66) 6.61 | (2.80) 2.75 |

TABLE 2-continued

| Comp. No. | m.p. (°C.) | Yield (%) | Elementary analysis or NMR |
|---|---|---|---|
| 9 | | 90.6 | 0.85 (3H, C̲H₃CH₂CH₂O—), 2.98 (6H, (CH₃)₂S—), 3.3–3.7 (2H, (CH₃)₂SC̲H₂—), 3.7–4.1 (3H, —C₆H₄—OC̲H₂C̲H—), 6.90, 7.50 (4H, —C₆H₄—O—), 10.09 (1H, CONH) |
| 10 | | 91.5 | 0.85 (3H, C̲H₃CH₂CH₂O—), 2.28 (3H, C̲H₃—C₆H₄—SO₃), 2.93 (6H, (CH₃)₂S—), 3.2–3.7 (2H, (CH₃)₂SC̲H₂—), 3.7–4.1 (3H, —C₆H₄—OC̲H₂C̲H—), 6.89, 7.50 (4H, —C₆H₄—O—), 7.12, 7.51 (4H, CH₃—C₆H₄—SO₃), 10.15 (1H, CONH) |

| Comp. No. | m.p. (°C.) | Yield (%) | For $C_{23}H_{30}N_4O_{13}S_2$ | | |
|---|---|---|---|---|---|
| | | | C | H | N |
| 11 | 117–119 | 96.2 | (43.53) 43.46 | (4.76) 4.64 | (8.83) 9.10 |

| Comp. No. | m.p. (°C.) | Yield (%) | Elementary analysis or NMR |
|---|---|---|---|
| 12 | | 90.5 | 1.07 (6H, (CH₃)₂ C̲HO—), 2.28 (3H, C̲H₃—C₆H₄—SO₃), 2.93 (6H, (CH₃)₂S—), 3.7–4.4 (3H, —C₆H₄—OC̲H₂C̲H—), 6.89, 7.50 (4H, —C₆H₄—O—), 7.11, 7.50 (4H, CH₃—C₆H₄—SO₃), |

TABLE 2-continued
| Comp. No. | m.p. (°C.) | Yield (%) | Elementary analysis or NMR |
|---|---|---|---|
10.14 (1H, CONH)
| 13 | | 91.1 | |
0.86 (3H, C<u>H</u>₃(CH₂)₃O—),  2.96 (6H, 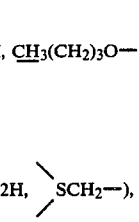),
3.3–3.7 (2H, 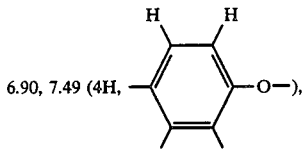),  3.7–4.2 (3H, 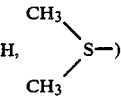),
6.90, 7.49 (4H, 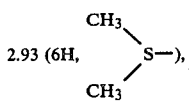),  10.09 (1H, CONH)
| 14 | | 96.6 | |
0.86 (3H, C<u>H</u>₃(CH₂)₃O—),  2.28 (3H, C<u>H</u>₃—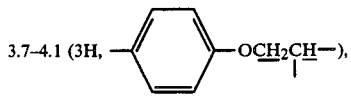—SO₃),
2.93 (6H, 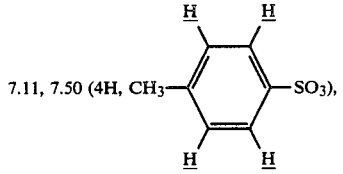),  3.3–3.7 (2H, 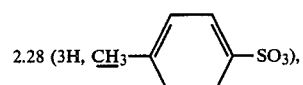),
3.7–4.1 (3H, 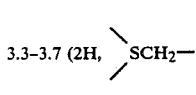),  6.89, 7.50 (4H, 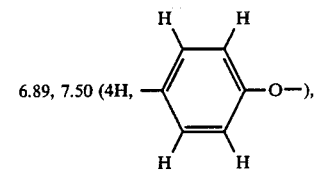),
7.11, 7.50 (4H, CH₃—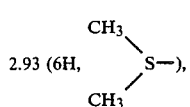—SO₃),  10.14 (1H, CONH)
| | | | For C₂₄H₃₂N₄O₁₃S₂·C₂H₅OH | | |
|---|---|---|---|---|---|
| | | | C | H | N |
| 15 | 106–108 | 93.5 | (44.95) | (5.51) | (8.06) |
| | | | 44.77 | 5.43 | 8.22 |
| 16 | | 90.1 | |
0.84 (3H, C<u>H</u>₃(CH₂)₅O—),  2.29 (3H, C<u>H</u>₃—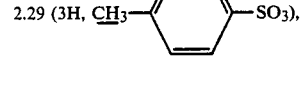—SO₃),
2.93 (6H, 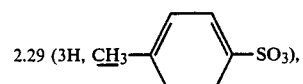),  3.7–4.2 (3H, —OC<u>H</u>₂CH—),

TABLE 2-continued

| Comp. No. | m.p. (°C.) | Yield (%) | Elementary analysis or NMR |
|---|---|---|---|

6.88, 7.50 (4H, —⬡—O—), 7.12, 7.50 (4H, CH₃—⬡—SO₃), 10.14 (1H, CONH)

| 17 | | 90.7 | |

1.0–2.0 (10H, —O—cyclohexyl), 2.93 (3H, C$\underline{H}_3$—⬡—SO₃), 2.93 (6H, (CH₃)₂S—), 3.7–4.2 (3H, —⬡—OC$\underline{H}_2$C$\underline{H}$—), 6.89, 7.50 (4H, —⬡—O—), 7.11, 7.50 (4H, CH₃—⬡—SO₃), 10.59 (1H, CONH)

| | | | For C$_{27}$H$_{33}$NO$_7$S$_2$ | | |
|---|---|---|---|---|---|
| | | | C | H | N |
| 18 | 132–133 | 91.3 | (59.21) | (6.07) | (2.56) |
| | | | 58.93 | 6.15 | 2.52 |

| | | | For C$_{23}$H$_{33}$NO$_7$S$_2$ | | |
|---|---|---|---|---|---|
| | | | C | H | N |
| 19 | 85–90 | 90.8 | (55.29) | (6.66) | (2.80) |
| | | | 55.15 | 6.51 | 2.75 |

| | | | For C$_{25}$H$_{37}$NO$_7$S$_2$ | | |
|---|---|---|---|---|---|
| | | | C | H | N |
| 20 | 107–108 | 91.5 | (56.90) | (7.07) | (2.65) |
| | | | 56.99 | 7.18 | 2.80 |

| 21 | | 91.0 | 1.10 (3H, C$\underline{H}_3$CH₂O—), 2.04 (3H, CH₃CO), |

2.28 (3H, CH₃—⬡—SO₃), 2.94 (6H, (CH₃)₂S—), 6.60–7.26 (4H, —⬡—H), 7.09, 7.50 (4H, CH₃—⬡—SO₃), 9.21 (1H, CONH)

TABLE 2-continued
| Comp. No. | m.p. (°C.) | Yield (%) | Elementary analysis or NMR |
|---|---|---|---|
| 22 | | 92.2 | 1.10 (3H, —OCH₂C*H*₃), 2.28 (3H, C*H*₃—⌬—SO₃), 2.29 (6H, (CH₃)₂S—), 6.70–8.10 (9H, —CO—⌬), 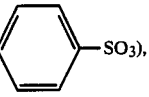, 7.10, 7.50 (4H, CH₃—⌬—SO₃), 9.24 (1H, CONH) |
| 23 | | 92.1 | 1.09 (3H, C*H*₃CH₂O—), 2.04 (3H, CH₃CO), 2.28 (3H, C*H*₃—⌬—SO₃), 2.92 (6H, (CH₃)₂S—), 6.94–7.17 (4H, ⌬), 7.09, 7.50 (4H, CH₃—⌬—SO₃), 10.24 (1H, CONH) |
| 24 | | 93.4 | 0.92 (3H, SCH₂CH₂C*H*₃), 1.14 (3H, —OCH₂C*H*₃), 2.28 (3H, C*H*₃—⌬—SO₃), 2.95 (3H, S—C*H*₃), 7.6–6.9 (9H, —COO—⌬, —NH—⌬—O—), 7.10, 7.49 (4H, CH₃—⌬—SO₃), 10.0 (1H, CONH) |
| | | | For C₂₅H₃₅NO₈S₂ | | |
|---|---|---|---|---|---|
| | | | C | H | N |
| 25 | 87–91 | 93.0 | (55.43) | (6.51) | (2.59) |
| | | | 55.23 | 6.61 | 2.35 |
| | | | For C₂₆H₃₇NO₉S₂ | | |
|---|---|---|---|---|---|
| | | | C | H | N |
| 26 | 90–92 | 91.0 | (54.62) | (6.52) | (2.45) |

TABLE 2-continued

| Comp. No. | m.p. (°C.) | Yield (%) | Elementary analysis or NMR | | |
|---|---|---|---|---|---|
| | | | 54.43 | 6.65 | 2.34 |
| | | | For C$_{30}$H$_{37}$NO$_8$S$_2$ | | |
| | | | C | H | N |
| 27 | 116-120 | 95.1 | (59.68) | (6.18) | (2.32) |
| | | | 59.52 | 6.20 | 2.30 |

| 28 | | 94.2 | 1.09 (3H, —OCH$_2$C<u>H</u>$_3$), 2.29 (3H, C<u>H</u>$_3$—C$_6$H$_4$—SO$_3$), 2.4–2.7 (4H, —OCOC<u>H</u>$_2$C<u>H</u>$_2$COOH), 2.93 (6H, (CH$_3$)$_2$S—), 4.07 (2H, —C$_6$H$_4$—OC<u>H</u>$_2$CH(CH$_3$)$_2$), 6.88, 7.51 (4H, NH—C$_6$H$_4$—O—), 7.12, 7.51 (4H, CH$_3$—C$_6$H$_4$—SO$_3$) |

| 29 | | 92.1 | 0.85 (3H, C<u>H</u>$_3$CH$_2$CH$_2$O—), 2.28 (3H, C<u>H</u>$_3$—C$_6$H$_4$—SO$_3$), 2.92 (6H, (CH$_3$)$_2$S—), 3.95 (3H, —C$_6$H$_4$—OC<u>H</u>$_2$C<u>H</u>—), 6.89, 7.50 (4H, —C$_6$H$_4$—O—), 7.12, 7.50 (4H, CH$_3$—C$_6$H$_4$—SO$_3$), 10.14 (1H, CONH) |

| | | | For C$_{29}$H$_{45}$NO$_7$S$_2$ | | |
| | | | C | H | N |
| 30 | 109-111 | 92.5 | (59.66) | (7.77) | (2.40) |
| | | | 59.92 | 8.00 | 2.45 |

| | | | For C$_{33}$H$_{53}$NO$_7$S$_2$ | | |
| | | | C | H | N |
| 31 | 90-93 | 90.6 | (61.94) | (8.35) | (2.19) |
| | | | 61.80 | 8.40 | 2.40 |

| | | | For C$_{25}$H$_{33}$NO$_9$S$_2$·½H$_2$O | | |
| | | | C | H | N |
| 32 | 94-95 | 90.5 | (53.17) | (6.07) | (2.48) |

TABLE 2-continued

| Comp. No. | m.p. (°C.) | Yield (%) | Elementary analysis or NMR | | |
|---|---|---|---|---|---|
| | | | 53.32 | 6.10 | 2.53 |
| | | | For $C_{31}H_4NO_9S_2$ | | |
| | | | C | H | N |
| 33 | 149–150 | 93.1 | (58.19) | (7.09) | (2.19) |
| | | | 58.10 | 7.01 | 2.03 |
| | | | For $C_{35}H_{37}NO_9S_2$ | | |
| | | | C | H | N |
| 34 | 135–138 | 90.3 | (61.84) | (5.49) | (2.06) |
| | | | 61.68 | 5.52 | 2.10 |

35 — 92.6

1.11 (3H, OCH$_2$C$\underline{H}_3$), 1.22 (3H, COOCH$_2$C$\underline{H}_3$), 1.38 (6H, $\underset{C\underline{H}_3CH_2}{\overset{C\underline{H}_3CH_2}{>}}$S—), 5.15 (1H, —OCH$_2$C$\underline{H}$CH$_2$O—), 6.7–7.2, 7.6–8.0 (4H, —H), 8.97 (1H, CONH)

36 — 91.8

1.09, 1.11 (3H, —OCH$_2$C$\underline{H}_3$), 1.21 (3H, —COOCH$_2$C$\underline{H}_3$), 1.35 (6H, $\underset{C\underline{H}_3CH_2}{\overset{C\underline{H}_3CH_2}{>}}$S—), 1.8–2.2 (2H, $>$SCH$_2$C$\underline{H}_2$CH$_2$—), 2.28 (3H, CH$_3$——SO$_3$), 2.60 (2H, $>$SC$\underline{H}_2$CH$_2$CH$_2$—), 3.67 (2H, OC$\underline{H}_2$CHC$\underline{H}_2$OCH$_2$), 5.14 (1H, —OCH$_2$C$\underline{H}$CH$_2$O—), 6.8–7.2, 7.6–8.0 (4H, 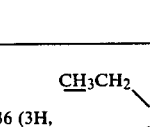—H), 7.10, 7.49 (4H, CH$_3$—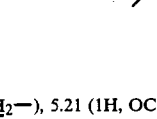—SO$_3$), 8.97 (1H, —CONH—)

37 — 93.3

1.03 (3H, —COCH$_2$C$\underline{H}_3$), 1.10 (3H, —OCH$_2$C$\underline{H}_3$), 1.36 (3H, $\underset{}{\overset{C\underline{H}_3CH_2}{>}}$S—), 2.92 (3H, $\underset{CH_3}{\overset{}{>}}$S—), 4.079 (2H, ——OC$\underline{H}_2$—), 5.21 (1H, OCH$_2$C$\underline{H}$—$\underset{OCOCH_2CH_3}{|}$), 6.5–6.7, 7.0–7.4 (4H, —H), 10.01 (1H, CONH)

TABLE 2-continued

| Comp. No. | m.p. (°C.) | Yield (%) | Elementary analysis or NMR |
|---|---|---|---|
| 38 | | 92.8 | 1.03 (3H, —COCH₂CH₃), 1.10 (3H, —OCH₂CH₃), 1.33 (3H, \SCH₂CH₃/), 1.8–2.2 (2H, \SCH₂CH₂/), 2.29 (3H, CH₃—⌬—SO₃), 2.89 (3H, \S—CH₃/), 4.07 (2H, —⌬—OCH₂—), 5.206 (1H, —OCH₂CHCH₂O—), 6.5–6.7, 7.0–7.4 (4H, aromatic H), 7.11, 7.50 (4H, CH₃—⌬—SO₃), 10.05 (1H, CONH) |
| 39 | | 91.4 | 1.09 (3H, CH₃CH₂—), 2.03 (3H, CH₃CO), 2.28 (3H, CH₃—⌬—SO₃), 2.89 (6H, (CH₃)₂S—), 3.1–3.5 (2H, \SCH₂/), 4.07 (2H, —⌬—OCH₂—), 5.0–5.2 (1H, —⌬—OCH₂CH—), 6.88, 7.50 (4H, —⌬—O—), 9.92 (1H, CONH) |
| 40 | | 90.1 | 2.28 (3H, CH₃—⌬—), 3.05 (6H, (CH₃)₂S—), 3.3–4.2 (4H, —⌬—OCH₂CHCH₂—), 3.79 (2H, \SCH₂CH₂—/), 4.43 (2H, \SCH₂CH₂—/), 6.7–7.2 (4H, —O—⌬—O—) |

TABLE 2-continued

| Comp. No. | m.p. (°C.) | Yield (%) | Elementary analysis or NMR |
|---|---|---|---|

7.10, 7.50 (4H, CH₃—[benzene ring with H's]—SO₃),

| | | | For C₁₉H₂₃N₃O₁₃S₂ | | |
|---|---|---|---|---|---|
| | | | C | H | N |
| 41 | 124–125 | 90.1 | (40.35) | (4.10) | (7.43) |
| | | | 40.38 | 4.10 | 7.40 |

| 42 | | 91.5 | 2.28 (3H, CH₃—[phenyl]—SO₃), 2.98 (6H, (CH₃)₂S—), 3.6–4.2 (9H, \SCH₂CH₂O—[phenyl]—OCH₂CHCH₂ (with I)), 6.4–6.8 (3H, —O—[benzene with H's]—H, H, O—), 7.0–7.4 (1H, —O—[phenyl]—O—), 7.11, 7.48 (4H, CH₃—[benzene]—SO₃), |

| | | | For C₁₉H₂₃N₃O₁₃S₂ | | |
|---|---|---|---|---|---|
| | | | C | H | N |
| 43 | 137–138 | 91.2 | (40.35) | (4.10) | (7.43) |
| | | | 40.15 | 4.16 | 7.43 |

| | | | For C₂₀H₂₈O₇S₂ | |
|---|---|---|---|---|
| | | | C | H |
| 44 | 116–117 | 90.5 | (54.04) | (6.35) |
| | | | 54.25 | 6.31 |

| | | | For C₂₁H₃₀O₇S₂ | |
|---|---|---|---|---|
| | | | C | H |
| 45 | 88–91 | 90.4 | (55.00) | (6.59) |
| | | | 54.85 | 6.37 |

| | | | For C₂₂H₃₂O₇S₂ | |
|---|---|---|---|---|
| | | | C | H |
| 46 | 105–107 | 91.7 | (55.91) | (6.82) |
| | | | 55.75 | 6.75 |

| | | | For C₂₃H₃₄O₇S₂ | |
|---|---|---|---|---|
| | | | C | H |
| 47 | 105–106 | 93.1 | (56.77) | (7.04) |
| | | | 56.50 | 7.01 |

| 48 | | 90.2 | 1.08 (3H, CH₃CH₂O—), 2.28 (3H, CH₃—[phenyl]—SO₃), 2.98 (6H, (CH₃)₂S—), |

TABLE 2-continued

| Comp. No. | m.p. (°C.) | Yield (%) | Elementary analysis or NMR |
|---|---|---|---|

3.76 (2H, $\diagup$SCH$_2$—) 3.8-4.0 (3H, —C$_6$H$_4$—O$\underline{CH}_2$C$\underline{H}$—), 6.91 (4H, —O—C$_6$H$_4$—O), 7.11 7.49 (4H, CH$_3$—C$_6$H$_4$—SO$_3$),

| | | | For C$_{25}$H$_{36}$O$_8$S$_2$ | |
|---|---|---|---|---|
| | | | C | H |
| 49 | 85-90 | 92.2 | (56.80) | (6.86) |
| | | | 56.55 | 6.92 |

| | | | For C$_{19}$H$_{25}$O$_4$SI | |
|---|---|---|---|---|
| | | | C | H |
| 50 | 112-112.8 | 93.5 | (47.91) | (5.29) |
| | | | 47.75 | 5.23 |

| | | | For C$_{26}$H$_{32}$O$_7$S$_2$ | |
|---|---|---|---|---|
| | | | C | H |
| 51 | 88-90 | 89.3 | (59.98) | (6.20) |
| | | | 59.98 | 6.24 |

| | | | For C$_{24}$H$_{36}$O$_7$S$_2$ | |
|---|---|---|---|---|
| | | | C | H |
| 52 | 126-128 | 91.5 | (57.58) | (7.25) |
| | | | 57.45 | 7.12 |

| | | | For C$_{26}$H$_{40}$O$_7$S$_2$ | |
|---|---|---|---|---|
| | | | C | H |
| 53 | 123-125 | 90.9 | (59.06) | (7.63) |
| | | | 58.91 | 7.75 |

| | | | For C$_{21}$H$_{29}$NO$_8$S$_2$ | | |
|---|---|---|---|---|---|
| | | | C | H | N |
| 54 | 134-136 | 91.2 | (51.73) | (5.99) | (2.87) |
| | | | 51.88 | 5.95 | 2.96 |

| | | | For C$_{24}$H$_{32}$O$_9$S$_2$ | |
|---|---|---|---|---|
| | | | C | H |
| 55 | 88-89 | 91.5 | (54.53) | (6.10) |
| | | | 54.48 | 6.02 |

| | | | For C$_{34}$H$_{36}$O$_9$S$_2$ | |
|---|---|---|---|---|
| | | | C | H |
| 56 | 108-110 | 92.3 | (62.56) | (5.46) |
| | | | 62.28 | 5.47 |

| | | | For C$_{20}$H$_{28}$O$_6$S$_2$ | |
|---|---|---|---|---|
| | | | C | H |
| 57 | 118-119 | 90.6 | (56.05) | (6.59) |
| | | | 56.23 | 6.39 |

| | | | For C$_{20}$H$_{28}$O$_6$S$_2$·½H$_2$O | |
|---|---|---|---|---|
| | | | C | H |
| 58 | 114-115 | 91.2 | (54.90) | (6.68) |
| | | | 54.91 | 6.68 |

TABLE 2-continued

| Comp. No. | m.p. (°C.) | Yield (%) | Elementary analysis or NMR |
|---|---|---|---|
| 59 | | 90.4 | 1.11 (3H, —OCH₂C<u>H</u>₃), 2.0–2.3 (2H, —CH₂C<u>H</u>₂CH₂O), 2.938 (6H, (CH₃)₂S—), 4.098 (2H, —O—C₆H₄—OC<u>H</u>₂CH₂O—), 5.04 (1H, —CH₂C<u>H</u>CH₂—O<u>H</u>), 6.89 (4H, —O—C₆H₄—O—) |
| 60 | 114–116 | 92.0 | For C₂₃H₃₄O₇S₂: C (56.77) 6.89; H (7.04) 6.91 |
| 61 | | 91.2 | 1.16 (3H, >SCH₂CH₂C<u>H</u>₃), 1.13, 1.09 (6H, —OCH₂C<u>H</u>₃, —COCH₂C<u>H</u>₃), 2.12 (2H, >SCH₂C<u>H</u>₂CH₂—), 3.4–4.3 (8H, —OC<u>H</u>₂CHC<u>H</u>₂OC<u>H</u>₂CH₃, OCOC<u>H</u>₂CH₃), 3.55 (2H, >SC<u>H</u>₂CH₂CH₂—), 4.40 (2H, >SCH₂CH₂C<u>H</u>₂—), 5.30 (1H, —OCH₂C<u>H</u>CH₂O—), 6.3–7.3 (4H, —O—C₆H₄—O—), 7.10 7.50 (4H, CH₃—C₆H₄—SO₃) |
| 62 | | 92.7 | 1.09 (3H, C<u>H</u>₃CH₂O—), 2.28 (3H, C<u>H</u>₃—C₆H₄—SO₃), 2.93 (6H, (CH₃)₂S—), 2.7–3.1 (2H, >SCH₂C<u>H</u>₂—), 3.30 (3H, C<u>H</u>₃OCH₂CO—), 4.06 (2H, CH₃OC<u>H</u>₂CO—), 4.09 (2H, —C₆H₄—OC<u>H</u>₂CHCH₂—), 5.1–5.4 (1H, —C₆H₄—OCH₂C<u>H</u>CH₂—) |

TABLE 2-continued

| Comp. No. | m.p. (°C.) | Yield (%) | Elementary analysis or NMR |
|---|---|---|---|
| | | | 6.91, 7.50 (4H, —CONH—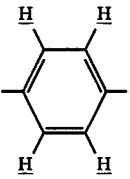—O—), 7.11 7.50 (4H, CH₃—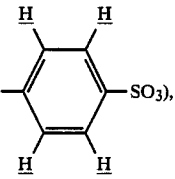—SO₃), |
| | | | 10.15 (1H, CONH) |
| 63 | | 89.3 | 0.94 (3H, C$\underline{H}$₃CH₂CH₂CH₂—S—), 1.86 (3H, CH₃CO), 2.8–3.1 (2H, \SCH₂C$\underline{H}$₂—/), |
| | | | 2.99 (3H, CH₃\S—/), 3.29 (3H, CH₃O—), 3.85 (2H, CH₃CONHC$\underline{H}$₂CO—), |
| | | | 4.08 (2H, 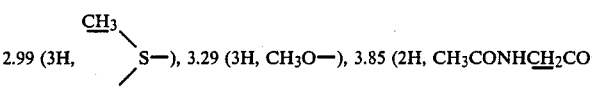OC$\underline{H}$₂CHCH₂—), 5.0–5.3 (1H, 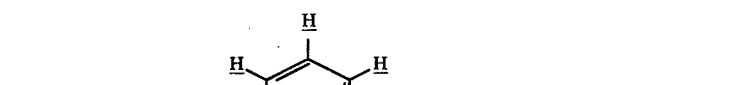OCH₂C$\underline{H}$CH₂—), |
| | | | 6.5–6.8, 7.0–7.4 (4H, CONH—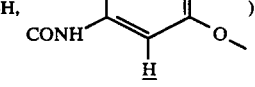—O—), 8.32 (1H, CH₃CON$\underline{H}$), |
| | | | 10.22 (1H, \SCH₂CH₂CON$\underline{H}$—/), |
| 64 | | 92.5 | 0.92 (3H, C$\underline{H}$₃CH₂CH₂CH₂—S—), 1.86 (3H, CH₃CO), 2.29 (3H, C$\underline{H}$₃—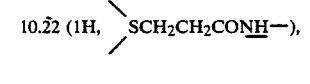—SO₃), |
| | | | 2.8–3.1 (2H, \SCH₂C$\underline{H}$₂—/), 2.95 (3H, CH₃\S—/), 3.28 (3H, CH₃O—), |
| | | | 3.85 (2H, CH₃CONHC$\underline{H}$₂CO—), 4.08 (2H, 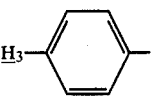OC$\underline{H}$₂CHCH₂—), |
| | | | 5.0–5.3 (1H, 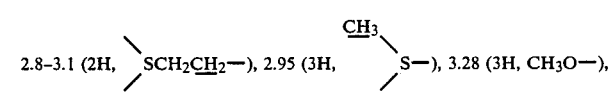OCH₂C$\underline{H}$CH₂—), |
| | | | 6.5–6.8, 7.0–7.4 (4H, —CONH—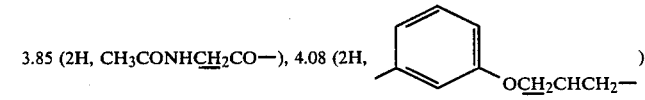—O—), 7.12 7.52 (4H, CH₃—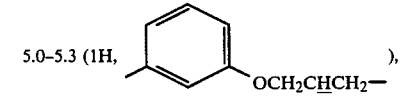—SO₃), |

TABLE 2-continued

| Comp. No. | m.p. (°C.) | Yield (%) | Elementary analysis or NMR |
|---|---|---|---|

8.35 (1H, CH₃CON*H*), 10.29 (1H, \SCH₂CH₂CON*H*)

---

| 65 | | 90.2 | |

0.93 (3H, C*H*₃CH₂CH₂CH₂O—), 1.11 (6H, CH₃CH₂C*H*₂\S—/CH₃CH₂C*H*₂), 3.02 (2H, \SCH₂C*H*₂—/), 4.0–4.3 (2H, —OC*H*₂CHCH—⌬), 4.82 (2H, ⌬—OC*H*₂CO—), 5.3–5.6 (1H, —OCH₂C*H*CH₂—⌬), 6.7–7.4 (5H, ⌬—O—), 6.7–7.2, 7.7–7.9 (4H, CONH—⌬(H,H,H,H)—*H*), 9.10 (1H, CONH)

---

| 66 | | 94.7 | |

0.93 (3H, C*H*₃CH₂CH₂CH₂O—), 1.11 (6H, CH₃CH₂C*H*₂\S—/CH₃CH₂C*H*₂), 2.28 (3H, C*H*₃—⌬—SO₃), 2.96 (2H, \SCH₂C*H*₂—/), 4.1–4.3 (2H, —OC*H*₂CHCH₂—⌬), 4.81 (2H, ⌬—OC*H*₂CO—), 5.2–5.6 (1H, —OCH₂C*H*CH₂—⌬), 6.7–7.4 (5H, ⌬—O—), 6.7–7.2, 7.7–7.9 (4H, CONH—⌬(H,H,H,H)—*H*),

TABLE 2-continued

| Comp. No. | m.p. (°C.) | Yield (%) | Elementary analysis or NMR |
|---|---|---|---|
| | | | 7.11, 7.48 (4H, CH$_3$—C$_6$H$_4$—SO$_3$), 9.15 (1H, CONH) |
| 67 | | 90.6 | 1.00 (3H, CH$_3$CH$_2$CH$_2$—S—), 2.20 (3H, CH$_3$—C$_6$H$_4$—), 2.90 (3H, CH$_3$-S(CH$_3$)—) 3.60 (2H, —C$_6$H$_4$—OCH$_2$CHCH$_2$—), 5.20 (1H, —C$_6$H$_4$—OCH$_2$CHCH$_2$—), 7.00, 7.30 (4H, CH$_3$—C$_6$H$_4$—SO$_3$), 7.0–7.6 (4H, CONH—C$_6$H$_4$—O—), 7.40 (10H, 2(OCOOCH$_2$—C$_6$H$_5$)), 10.05 (1H, CONH) |
| 68 | | 91.0 | 0.88 (12H, 2((CH$_3$)$_2$CH—)), 1.30 (3H, CH$_3$CH$_2$—S—), 2.30 (3H, CH$_3$—C$_6$H$_4$—SO$_3$), 2.90 (3H, CH$_3$-S(CH$_3$)—), 3.8 (2H, —C$_6$H$_4$—OCH$_2$CHCH$_2$—), 5.20 (1H, —C$_6$H$_4$—OCH$_2$CHCH$_2$—), 6.80, 7.40 (4H, CONH—C$_6$H$_4$—O—), 7.20, 7.40 (4H, CH$_3$—C$_6$H$_4$—SO$_3$), 9.80 (1H, CONH) |

TABLE 2-continued

| Comp. No. | m.p. (°C.) | Yield (%) | Elementary analysis or NMR |
|---|---|---|---|
| 69 | | 92.2 | 1.24 (3H, CH₃CHCO—, OH), 1.35 (6H, CH₃CH₂\S—, CH₃CH₂/), <br><br>2.28 (3H, CH₃—C₆H₄—SO₃), 2.3–2.6 (2H, \SCH₂CH₂CH₂—/), <br><br>4.34 (2H, —C₆H₄—OCH₂CHCH₂—), 5.2–5.5 (1H, —C₆H₄—OCH₂CHCH₂—), <br><br>6.8–7.6 (5H, —OCONH—C₆H₄—H), 6.86, 7.46 (4H, CONH—C₆H₄—O—), <br><br>7.10, 7.48 (4H, CH₃—C₆H₄—SO₃), 9.68 (1H, —OCONH—C₆H₅), <br><br>9.92 (1H, —CONH—C₆H₄—O—) |
| 70 | | 91.6 | 1.0–1.5 (9H, CH₃CH₂\S—, CH₃CH₂/, CH₃CH₂O—), <br><br>2.28 (3H, CH₃—C₆H₄—SO₃), 2.4–2.7 (2H, \SCH₂CH₂CH₂—/), <br><br>3.1–4.2 (13H, CH₃CH₂\SCH₂CH₂CH₂—C₆H₄—, CH₃CH₂/  OCH₂CHCH₂—, CH₃CH₂O—), <br><br>6.5–7.6 (13H, CONH—C₆H₄—, —OCH₂—C₆H₄—, CH₃—C₆H₄—SO₃) |
| 71 | | 92.0 | 0.92 (3H, CH₃CH₂CH₂CH₂—S—), 1.2–1.8 (4H, CH₃CH₂CH₂CH₂—S—), |

TABLE 2-continued

| Comp. No. | m.p. (°C.) | Yield (%) | Elementary analysis or NMR |
|---|---|---|---|

2.0 (2H, \SCH₂C̲H₂CH₂—), 2.88 (2H, \SCH₂CH₂C̲H₂—), 2.90 (3H, CH₃\S—), 3.1–3.6 (4H,

CH₃CH₂CH₂C̲H₂\SC̲H₂CH₂CH₂—), 3.7–5.0 (9H, —OC̲H₂C̲HC̲H₂— / OC̲H₂OC̲H₂— phenyl), 6.7–8.0 (14H, CONH—phenyl—H̲, —O—phenyl—H̲, —OCH₂—phenyl—H̲)

| 72 | 74–76 | 95.2 | |

0.81 (3H, C̲H₃CH₂CH₂NH—), 2.20 (3H, C̲H₃—phenyl—SO₃), 2.90 (6H, CH₃\S—CH₃), 3.30 (3H, C̲H₃COCH₂CO—), 3.50 (2H, —phenyl—OCH₂CHC̲H₂—), 5.20 (1H, —phenyl—OCH₂C̲HCH₂—), 6.5–7.5 (4H, CONH—phenyl—H̲), 7.20, 7.40 (4H, CH₃—phenyl—SO₃), 10.20 (2H, —CON̲H—phenyl—, —CON̲HCH₂CH₂CH₃)

| | | | For C₂₅H₃₅NO₈S₂ |
| | | | C | H | N |
| 73 | 112–114 | 92.0 | (55.43) | (6.51) | (2.59) |
| | | | 55.21 | 6.84 | 2.36 |

TABLE 2-continued
| Comp. No. | m.p. (°C.) | Yield (%) | Elementary analysis or NMR |
|---|---|---|---|
| 74 | | 90.4 | 1.10 (3H, C̲H₃CH₂O—), 2.28 (3H, C̲H₃——SO₃), 2.93 (6H, (C̲H₃)₂S—), 2.8–3.1 (2H, ＼SCH₂C̲H₂—／), 3.4–3.7 (3H, ——OCH₂C̲HC̲H₂OH), 6.90, 7.50 (4H, —CONH—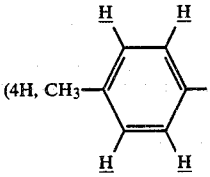—O—), 7.12, 7.51 (4H, CH₃—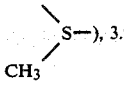—SO₃), 10.14 (1H, CONH) |
| 75 | | 90.0 | 0.92 (3H, C̲H₃CH₂CH₂CH₂—S—), 2.59 (2H, ＼SCH₂CH₂C̲H₂—／), 2.93 (3H, ＼S—／CH₃), 3.9–4.4 (5H, —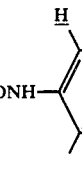—OC̲H₂C̲HCH₂—), 6.7–8.0 (9H, —O—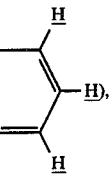—H̲), —CONH——H̲), 9.15 (1H, CONH) |
| 76 | | 90.2 | 0.87 (3H, C̲H₃CH₂CH₂CH₂O—), 1.03 (6H, (C̲H₃CH₂CH₂)₂S—), 3.09 (2H, ＼SCH₂C̲H₂—／), 3.8–4.2 (3H, —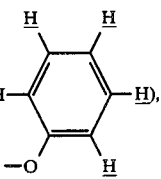—OC̲H₂C̲H—), 6.7–7.2, 7.8–8.1 (4H, —CONH——H̲), —O—), 9.32 (1H, CONH) |
| 77 | | 90.6 | 0.92 (3H, C̲H₃CH₂CH₂CH₂O—), 1.00 (6H, (C̲H₃CH₂CH₂)₂S—), |

TABLE 2-continued

| Comp. No. | m.p. (°C.) | Yield (%) | Elementary analysis or NMR |
|---|---|---|---|

2.28 (3H, C$\underline{H}$$_3$—⟨phenyl⟩—SO$_3$), 3.10 (2H, ⟩SCH$_2$C$\underline{H}$$_2$—), 3.8–4.2 (3H, ⟨methylphenyl⟩—OC$\underline{H}$$_2$C$\underline{H}$—), 6.7–7.2, 7.8–8.1 (4H, —CONH—⟨phenoxy ring, H positions⟩$\underline{H}$), 7.11, 7.52 (4H, CH$_3$—⟨phenyl⟩—SO$_3$), 9.37 (1H, CONH)

---

Given below are examples of pharmacological compositions prepared by using the compounds of the present invention.

Preparation 1: Tablets

Tablets were prepared from the following composition (300 mg per tablet).

| | |
|---|---|
| Compound 20 | 100 mg |
| Lactose | 47 mg |
| Corn starch | 50 mg |
| Crystalline cellulose | 50 mg |
| Hydroxypropyl cellulose | 15 mg |
| Talc | 2 mg |
| Magnesium stearate | 2 mg |
| Ethyl cellulose | 30 mg |
| Fatty acid glyceride | 2 mg |
| Titanium dioxide | 2 mg |
| Total: | 300 mg |

Preparation 2: Granules

A granular preparation was formulated from the following composition (1000 mg per wrapper).

| | |
|---|---|
| Compound 19 | 200 mg |
| Mannitol | 540 mg |
| Corn starch | 100 mg |
| Crystalline cellulose | 100 mg |
| Hydroxypropyl cellulose | 50 mg |
| Talc | 10 mg |
| Total: | 1000 mg |

Preparation 3: Particles

A particulate preparation was formulated from the following composition (1000 mg per wrapper).

| | |
|---|---|
| Compound 7 | 200 mg |
| Mannitol | 520 mg |
| Corn starch | 100 mg |
| Crystalline cellulose | 100 mg |
| Hydroxypropyl cellulose | 70 mg |
| Talc | 10 mg |
| Total: | 1000 mg |

Preparation 4: Capsules

An encapsulated preparation was formulated from the following composition (250 mg per capsule).

| | |
|---|---|
| Compound 25 | 100 mg |
| Lactose | 50 mg |
| Corn starch | 47 mg |
| Crystalline cellulose | 50 mg |
| Talc | 2 mg |
| Magnesium stearate | 1 mg |
| Total: | 250 mg |

Preparation 5: Syrup

A 100 ml quantity of syrup was prepared from the following composition.

| | |
|---|---|
| Compound 8 | 1 g |
| Purified white sugar | 60 g |
| Ethyl p-hydroxybenzoate | 5 mg |
| Butyl p-hydroxybenzoate | 5 mg |
| Flavour | Adequate amount |
| Coloring agent | Adequate amount |
| Purified water | Adequate amount |
| Total: | 100 ml |

Preparation 6: Injection solution

An injection solution was prepared from the following composition (2 ml per ampule).

| | |
|---|---|
| Compound 4 | 100 mg |
| Distilled water for injection | Adequate amount |
| Total: | 2 ml |

Preparation 7: Suppositories

Suppositories were prepared from the following composition (1500 mg per piece).

| | |
|---|---|
| Compound 32 | 100 mg |
| Fatty acid glyceride | 1400 mg |
| (available under the trademark "Witepsol W-35", product of Dynamit Nobel A. G., West Germany) | |
| Total: | 1500 mg |

Preparation 8: Inhalant

A 10 g quantity of inhalant was prepared from the following composition.

| | |
|---|---|
| Compound 10 | 100 mg |
| Sorbitan monooleate | 10 mg |
| Flon 12 | 9890 mg |
| Total: | 10 g |

Preparation 9: Tablets

Tablets were prepared from the following composition (300 mg per tablet).

| | |
|---|---|
| Compound 45 | 100 mg |
| Lactose | 47 mg |
| Corn starch | 50 mg |
| Crystalline cellulose | 50 mg |
| Hydroxypropyl cellulose | 15 mg |
| Talc | 2 mg |
| Magnesium stearate | 2 mg |
| Ethyl cellulose | 30 mg |
| Fatty acid glyceride | 2 mg |
| Titanium dioxide | 2 mg |
| Total: | 300 mg |

Preparation 10: Granules

A granular preparation was prepared from the following composition (1000 mg per wrapper).

| | |
|---|---|
| Compound 44 | 200 mg |
| Mannitol | 540 mg |
| Corn starch | 100 mg |
| Crystalline cellulose | 100 mg |
| Hydroxypropyl cellulose | 50 mg |
| Talc | 10 mg |
| Total: | 1000 mg |

Preparation 11: Particles

A particulate preparation was prepared from the following composition (1000 mg per wrapper).

| | |
|---|---|
| Compound 51 | 200 mg |
| Mannitol | 520 mg |
| Corn starch | 100 mg |
| Crystalline cellulose | 100 mg |
| Hydroxypropyl cellulose | 70 mg |
| Talc | 10 mg |
| Total: | 1000 mg |

Preparation 12: Capsules

A encapsulated preparation was formulated from the following composition (250 mg per capsule).

| | |
|---|---|
| Compound 46 | 100 mg |
| Lactose | 50 mg |
| Corn starch | 47 mg |
| Crystalline cellulose | 50 mg |
| Talc | 2 mg |
| Magnesium stearate | 1 mg |
| Total: | 250 mg |

Preparation 13: Syrup

A 100 ml quantity of syrup was prepared from the following composition.

| | |
|---|---|
| Compound 42 | 1 g |
| Purified white sugar | 60 g |
| Ethyl p-hydroxybenzoate | 5 mg |
| Butyl p-hydroxybenzoate | 5 mg |
| Flavour | Adequate amount |
| Coloring agent | Adequate amount |
| Purified water | Adequate amount |
| Total: | 100 ml |

Preparation 14: Injection solution

An injection solution was prepared from the following composition (2 ml per ampule).

| | |
|---|---|
| Compound 48 | 100 mg |
| Distilled water for injection | Adequate amount |
| Total: | 2 ml |

Preparation 15: Suppositories

Suppositories were prepared from the following composition (1500 mg per piece).

| | |
|---|---|
| Compound 47 | 100 mg |
| Fatty acid glyceride | 1400 mg |
| (available under the trademark "Witepsol W-35", product of Dynamit Nobel A. G., West Germany.) | |
| Total: | 1500 mg |

Preparation 16: Inhalant

A 10 g quantity of inhalant was prepared from the following composition.

| | |
|---|---|
| Compound 60 | 100 mg |
| Sorbitan monooleate | 10 mg |
| Flon 12 | 9890 mg |
| Total: | 10 g |

Compounds of this invention were tested for pharmacological activity and acute toxicity, with the following results.

(1) Effect on passive cutaneous anaphylaxis (PCA)

A homocytotropic antibody for use in this test was produced according to the method of Tada et al. (Journal of Immunology 106, 1002 (1971)) by immunizing a Wister rat with DNP-As (a product prepared by coupling dinitrophenyl group to an extract of Ascaris suum) and with pertussis vaccine. A serum containing the homocytotropic antibody was intracutaneously injected at four points of the shaven back of the male Wister rats weighing 180 to 200 g. Fourty-eight hours after the injection, a physiological saline containing 2.0 mg of DNP-As and 2.5 mg of Evans Blue to induce response, and the rats were dehematized to death in 30 minutes. The amount of the effusion of the dye was measured according to the method of Katayama et al (Microbiology and Immunology 22, 89 (1978)) and the measured values were used as an index for PCA. The present compounds were administered to the rats 1 hour prior to the antigen challenge. Table 3 below shows the results.

TABLE 3

| Comp. No. | Dose (mg/Kg) | PCA Inhibition (%) |
|---|---|---|
| 4 | 50 | 48.8 |
| 7 | 100 | 57.0 |
| 8 | 20 | 57.0 |
| 10 | 100 | 47.0 |
| 17 | 100 | 47.0 |
| 18 | 100 | 34.0 |
| 19 | 10 | 51.6 |
| 20 | 50 | 35.1 |
| 25 | 100 | 63.6 |
| 29 | 50 | 46.2 |
| 32 | 10 | 47.0 |
| 40 | 200 | 53.2 |
| 42 | 200 | 58.4 |
| 44 | 200 | 57.0 |
| 45 | 200 | 59.0 |
| 46 | 100 | 64.8 |
| 47 | 50 | 39.2 |
| 48 | 20 | 48.0 |
| 49 | 20 | 42.5 |
| 51 | 100 | 56.7 |
| 52 | 100 | 53.3 |
| 54 | 20 | 51.8 |
| 55 | 50 | 55.2 |
| 56 | 100 | 44.7 |

(2) Acute toxicity test

Male ddy mice weighing about 20 g were used. A solution of the compound in physiological saline was injected intraperitoneally. The dose lethal to 50% of mice was determined by the up-down method. The results are shown in Table 4.

TABLE 4

| Comp. No. | LD$_{50}$ (mg/Kg) |
|---|---|
| 4 | 1040 |
| 7 | 359 |
| 8 | 254 |
| 10 | 171 |
| 17 | 93.6 |
| 18 | 112.5 |
| 19 | 254 |
| 20 | 179 |
| 25 | 233 |
| 29 | 75.2 |
| 32 | 366 |
| 40 | 283 |
| 42 | 231 |
| 44 | 352 |
| 45 | 302 |
| 47 | 293 |
| 48 | 302 |
| 49 | 221 |
| 51 | 150.5 |
| 52 | 132 |
| 54 | 327 |
| 55 | 291 |

TABLE 4-continued

| Comp. No. | LD$_{50}$ (mg/Kg) |
|---|---|
| 56 | 85 |

We claim:

1.

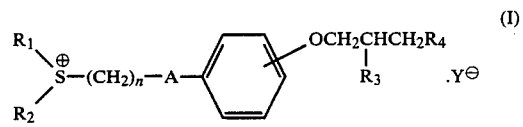

wherein $R_1$ and $R_2$ are the same or different and are each alkyl having 1 to 6 carbon atoms; $R_3$ is hydrogen, hydroxy, alkoxy having 1 to 6 carbon atoms, phenylalkyloxy having 7 to 10 carbon atoms, or phenylalkyloxymethoxy having 8 to 11 carbon atoms; $R_4$ is hydrogen, hydroxy, alkoxy having 1 to 6 carbon atoms, acyloxy having 2 to 6 carbon atoms, cycloalkyloxy having 5 to 7 carbon atoms, phenoxy, benzoyloxy, alkoxycarbonyloxy having 2 to 5 carbon atoms, ethoxy substituted with alkoxy having 1 to 6 carbon atoms, carbamoyloxy, alkylcarbamoyloxy having 2 to 5 carbon atoms, phenylcarbamoyloxy or phenylalkyloxycarbonyloxy having 8 to 11 carbon atoms; Y is an acid residue; A is —CONH— and n is an integer of 1 to 3; with the proviso that $R_3$ and $R_4$ are not both hydrogen at the same time and that when $R_3$ is hydroxy, $R_4$ is not acyloxy having 2 to 6 carbon atoms.

2. A sulfonium compound as defined in claim 1 wherein $R_3$ is hydrogen, hydroxy, alkoxy having 1 to 6 carbon atoms, and $R_4$ is hydrogen, hydroxy, alkoxy having 1 to 6 carbon atoms, cycloalkyloxy having 5 to 7 carbon atoms, phenoxy, acyloxy having 2 to 6 carbon atoms, benzoyloxy, ethoxy substituted with $C_{1-6}$ alkoxy, or carbamoyloxy.

3. A sulfonium compound as defined in claim 1 wherein $R_3$ is phenylalkyloxy having 7 to 10 carbon atoms, or phenylalkyloxymethoxy having 8 to 11 carbon atoms; and $R_4$ is alkoxy having 1 to 6 carbon atoms, phenoxy, alkoxycarbonyloxy having 2 to 5 carbon atoms, phenylalkyloxycarbonyloxy having 8 to 11 carbon atoms, alkylcarbamoyloxy having 2 to 5 carbon atoms or phenylcarbamoyloxy.

4. A sulfonium compound as defined in claim 1 wherein Y is a residue of hydrogen chlorine, hydrogen iodide, hydrogen bromide, tetrafluoroboric acid, perchloric acid, phosphoric acid, sulfuric acid, nitric acid, metaphosphoric acid, methanesulfonic acid, benzenesulfonic acid, toluenesulfonic acid, camphorsulfonic acid, 1,5-naphtalenedisulfonic acid, picrylsulfonic acid, cyclohexylsulfamic acid, lactic acid, maleic acid, malonic acid, fumaric acid, butyric acid, ascorbic acid, linoleic acid, lauric acid, palmitic acid, stearic acid, oleic acid, propionic acid, citric acid, acetic acid, formic acid, nicotinic acid or succinic acid.

5. A sulfonium compound as defined in claim 1 wherein $R_3$ and $R_4$ are the same or different and each represent hydroxy, alkoxy having 1 to 6 carbon atoms or acyloxy having 2 to 6 carbon atoms.

6. A compound as defined in claim 1 which is a compound of the formula

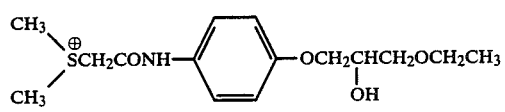

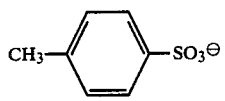

7. A compound as defined in claim 1 which is a compound of the formula

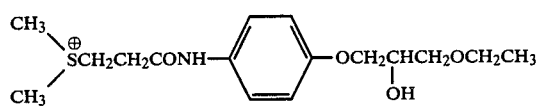

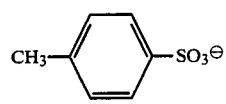

8. A compound as defined in claim 1 which is a compound of the formula

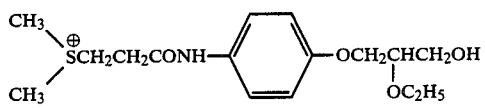

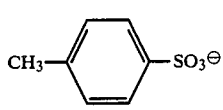

9. An anti-allergic composition comprising as an active component a sulfonium compound represented by the formula

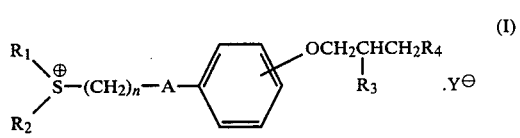

wherein $R_1$, $R_2$, $R_3$, $R_4$, n, A and Y are as defined in claim 1 in admixture with a pharmaceutically acceptable, non-toxic carrier or excipient.

* * * * *